US010799129B2

(12) United States Patent
Shiono et al.

(10) Patent No.: US 10,799,129 B2
(45) Date of Patent: Oct. 13, 2020

(54) BIOLOGICAL INFORMATION MEASURING DEVICE INCLUDING LIGHT SOURCE, LIGHT DETECTOR, AND CONTROL CIRCUIT

(71) Applicant: Panasonic Intellectual Property Management Co., Ltd., Osaka (JP)

(72) Inventors: Teruhiro Shiono, Osaka (JP); Takamasa Ando, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 317 days.

(21) Appl. No.: 15/391,179

(22) Filed: Dec. 27, 2016

(65) Prior Publication Data

US 2017/0196467 A1    Jul. 13, 2017

(30) Foreign Application Priority Data

Jan. 7, 2016  (JP) .................................. 2016-001998
Jan. 7, 2016  (JP) .................................. 2016-001999
Oct. 21, 2016 (JP) .................................. 2016-207065

(51) Int. Cl.
*A61B 5/024*  (2006.01)
*A61B 5/026*  (2006.01)
(Continued)

(52) U.S. Cl.
CPC ............ *A61B 5/0261* (2013.01); *A61B 5/024* (2013.01); *A61B 5/14546* (2013.01);
(Continued)

(58) Field of Classification Search
CPC ... A61B 5/0261; A61B 5/024; A61B 5/14546; A61B 5/14552; A61B 5/6814; A61B 5/7221
See application file for complete search history.

(56) References Cited

U.S. PATENT DOCUMENTS 4,894,547 A * 1/1990 Leffell ................. A61B 5/0071
                                                          250/459.1
5,213,105 A * 5/1993 Gratton .............. A61B 5/14553
                                                          250/341.2
(Continued)

FOREIGN PATENT DOCUMENTS

CN       103153198 A    6/2013
CN       103354729 A    10/2013
(Continued)

OTHER PUBLICATIONS

Guillaume Lopez et al., "Continuous blood pressure monitoring in daily life", Journal of Advanced Mechanical Design, Systems, and Manufacturing vol. 4, No. 1, pp. 179-186, Feb. 26, 2010.
(Continued)

*Primary Examiner* — Joanne M Hoffman
(74) *Attorney, Agent, or Firm* — McDermott Will & Emery LLP

(57) ABSTRACT

A biological information measuring device according to an aspect of the present disclosure includes: a light source that, in operation, emits irradiation light for irradiating a test portion of a subject; a light detector that, in operation, detects light from the subject and outputs an electrical signal corresponding to the light; and a control circuit that, in operation, determines a power of the irradiation light emitted by the light source, and that, in operation, measures biological information related to a blood flow at the test portion based on the electrical signal. The control circuit, in operation, detects a distance between the light source and the test portion based on the electrical signal, and determines the power of the irradiation light such that the power of the irradiation light is increased as the distance increases.

18 Claims, 14 Drawing Sheets

(51) Int. Cl.
*A61B 5/1455* (2006.01)
*A61B 5/145* (2006.01)
*A61B 5/00* (2006.01)

(52) U.S. Cl.
CPC ........ *A61B 5/14552* (2013.01); *A61B 5/6814* (2013.01); *A61B 5/7221* (2013.01)

(56) References Cited

U.S. PATENT DOCUMENTS

| | | | | |
|---|---|---|---|---|
| 5,395,502 | A * | 3/1995 | Pawliszyn | G01N 21/4133 204/603 |
| 5,676,142 | A * | 10/1997 | Miwa | A61B 5/0091 600/309 |
| 5,747,789 | A * | 5/1998 | Godik | A61B 5/0059 250/208.1 |
| 6,062,216 | A * | 5/2000 | Corn | A61B 5/113 128/204.23 |
| 6,124,597 | A * | 9/2000 | Shehada | A61B 5/0075 250/458.1 |
| 6,542,763 | B1 * | 4/2003 | Yamashita | A61B 5/0059 600/310 |
| 6,584,342 | B1 * | 6/2003 | Trushin | A61B 5/0064 600/476 |
| 6,588,901 | B1 * | 7/2003 | Grinvald | A61B 3/1241 351/206 |
| 6,630,673 | B2 * | 10/2003 | Khalil | A61B 5/14532 250/341.8 |
| 7,228,166 | B1 * | 6/2007 | Kawasaki | A61B 5/0073 600/424 |
| 8,025,687 | B2 * | 9/2011 | Streeter | A61N 5/0618 607/88 |
| 9,839,365 | B1 * | 12/2017 | Homyk | A61B 5/489 |
| 2002/0068859 | A1 * | 6/2002 | Knopp | A61B 5/1455 600/322 |
| 2004/0215082 | A1 * | 10/2004 | Chance | A61B 5/0059 600/473 |
| 2005/0020926 | A1 * | 1/2005 | Wiklof | A61B 1/00193 600/476 |
| 2005/0187446 | A1 * | 8/2005 | Nordstrom | A61B 5/14551 600/323 |
| 2006/0098848 | A1 * | 5/2006 | Nagasaka | A61B 5/1172 382/124 |
| 2006/0129038 | A1 * | 6/2006 | Zelenchuk | A61B 5/14535 600/322 |
| 2006/0155348 | A1 * | 7/2006 | deCharms | A61N 5/0601 607/89 |
| 2006/0161055 | A1 * | 7/2006 | Pewzner | A61B 5/0059 600/310 |
| 2006/0184050 | A1 * | 8/2006 | Urano | A61B 5/0073 600/485 |
| 2006/0189861 | A1 * | 8/2006 | Chen | A61B 5/14553 600/331 |
| 2007/0299309 | A1 * | 12/2007 | Seibel | A61B 1/0008 600/117 |
| 2008/0021329 | A1 * | 1/2008 | Wood | A61B 5/0059 600/476 |
| 2009/0002485 | A1 * | 1/2009 | Fujiwara | G02B 7/004 348/80 |
| 2009/0062685 | A1 * | 3/2009 | Bergethon | A61B 5/0059 600/554 |
| 2009/0086896 | A1 * | 4/2009 | Boyden | G01N 23/223 378/44 |
| 2009/0086904 | A1 * | 4/2009 | Boyden | G01N 23/223 378/45 |
| 2009/0086905 | A1 * | 4/2009 | Boyden | G01N 23/223 378/46 |
| 2009/0131802 | A1 * | 5/2009 | Fulghum | A61B 5/0059 600/478 |
| 2009/0236541 | A1 * | 9/2009 | Lomnes | A61B 1/043 250/458.1 |
| 2009/0318815 | A1 * | 12/2009 | Barnes | A61B 5/742 600/473 |
| 2009/0326383 | A1 * | 12/2009 | Barnes | A61B 5/0059 600/476 |
| 2010/0013812 | A1 * | 1/2010 | Gu | G06F 3/014 345/207 |
| 2010/0191109 | A1 * | 7/2010 | Fukutani | A61B 5/0059 600/437 |
| 2010/0280398 | A1 * | 11/2010 | Hachiga | A61B 5/0285 600/504 |
| 2011/0013002 | A1 * | 1/2011 | Thompson | A61B 5/0059 348/77 |
| 2011/0243414 | A1 * | 10/2011 | Yamamoto | G06T 11/006 382/131 |
| 2011/0263955 | A1 * | 10/2011 | Narita | A61B 1/00165 600/341 |
| 2012/0150164 | A1 * | 6/2012 | Lee | A61B 18/02 606/16 |
| 2012/0289839 | A1 * | 11/2012 | Takenoshita | A61B 5/02125 600/480 |
| 2013/0102907 | A1 * | 4/2013 | Funane | A61B 5/0075 600/476 |
| 2013/0296717 | A1 | 11/2013 | Takenoshita et al. | |
| 2014/0002806 | A1 * | 1/2014 | Buchel | G01S 7/48 356/4.01 |
| 2014/0046152 | A1 * | 2/2014 | Bechtel | A61B 5/14551 600/323 |
| 2014/0074076 | A1 * | 3/2014 | Gertner | A61N 7/02 606/12 |
| 2014/0121636 | A1 * | 5/2014 | Boyden | A61M 5/427 604/506 |
| 2014/0276104 | A1 * | 9/2014 | Tao | A61B 5/7239 600/476 |
| 2014/0293091 | A1 * | 10/2014 | Rhoads | G01J 3/513 348/234 |
| 2014/0303454 | A1 * | 10/2014 | Clifton | A61B 5/0205 600/301 |
| 2015/0148623 | A1 * | 5/2015 | Benaron | A61B 5/0059 600/306 |
| 2015/0173618 | A1 | 6/2015 | Kusukame | |
| 2015/0190061 | A1 * | 7/2015 | Godavarty | A61B 5/02028 600/328 |
| 2015/0196200 | A1 * | 7/2015 | Fixler | A61K 49/0423 600/431 |
| 2015/0257659 | A1 * | 9/2015 | Broers | A61B 5/7203 600/473 |
| 2016/0174887 | A1 * | 6/2016 | Kirenko | A61B 5/14552 600/332 |
| 2016/0287088 | A1 * | 10/2016 | Case | A61B 5/015 |
| 2017/0079530 | A1 * | 3/2017 | DiMaio | A61B 5/0075 |
| 2017/0095170 | A1 * | 4/2017 | Verkruijsse | A61B 5/0064 |
| 2017/0142314 | A1 * | 5/2017 | Moore | H04N 5/2252 |
| 2017/0164904 | A1 * | 6/2017 | Kirenko | A61B 5/7214 |
| 2017/0202463 | A1 * | 7/2017 | Muhlsteff | A61B 5/02125 |
| 2017/0238842 | A1 * | 8/2017 | Jacquel | A61B 5/743 |
| 2018/0055364 | A1 * | 3/2018 | Pierro | A61B 5/0006 |
| 2018/0168454 | A1 * | 6/2018 | Ando | A61B 5/0075 |

FOREIGN PATENT DOCUMENTS

| | | | | |
|---|---|---|---|---|
| EP | 2438849 A1 * | 4/2012 | ........ | A61B 5/02416 |
| JP | 63-059930 | 3/1988 | | |
| JP | 2003-337102 | 11/2003 | | |
| JP | 2003337102 A * | 11/2003 | | |
| JP | 2008-284165 | 11/2008 | | |
| JP | 2009-136495 | 6/2009 | | |
| JP | 2015-134157 | 7/2015 | | |
| WO | 2005/082240 | 9/2005 | | |

OTHER PUBLICATIONS

English Translation of Chinese Search Report dated Aug. 7, 2020 for the related Chinese Patent Application No. 201611126774.4.

* cited by examiner

BIOLOGICAL INFORMATION MEASURING DEVICE INCLUDING LIGHT SOURCE, LIGHT DETECTOR, AND CONTROL CIRCUIT

BACKGROUND

1. Technical Field

The present disclosure relates to a technique that measures biological information.

2. Description of the Related Art

As basic parameters for determining the physical condition of a human, a heart rate, a blood flow rate, a blood pressure, an oxygen saturation in blood and others are widely used. These pieces of biological information on blood are usually measured by a contact measuring instrument. Since the body of a subject is restrained by a contact measuring instrument, when measurement is continuously made particularly for a long time, discomfort of the subject is caused.

Japanese Unexamined Patent Application Publication No. 2003-337102 has disclosed a biological activity measuring device including a head fixing unit that restricts movement of the head of a subject. The head fixing unit is, for instance, a jaw support base that fixes the jaw or forehead, or an eye mask. Since movement of the head is restricted in this configuration, brain functions can be measured accurately. In the case of continuous measurement, however, discomfort of a subject is caused.

In order to obtain biological information, near-infrared rays (electromagnetic waves in a wavelength range of approximately 700 nm to approximately 2500 nm) are often utilized. Among all, near-infrared rays particularly with a relatively short wavelength (for instance, approximately 950 nm or less) are often utilized. Such near-infrared rays have the property of penetrating a body tissue such as muscle, fat and bones with a relatively high transmittance, but on the other hand, have the property of being likely to be absorbed by oxyhemoglobin ($HbO_2$) and deoxyhemoglobin (Hb) in blood. As a method for measuring biological information utilizing such properties, a near-infrared spectroscopy (hereinafter referred to as "NIRS") is known. Utilizing the NIRS enables measurement of the oxyhemoglobin concentration and deoxyhemoglobin concentration in the blood in brain, for instance. The activity state (hereinafter sometimes called "brain function") of a brain can be estimated based on an oxygenation state of hemoglobin.

Japanese Unexamined Patent Application Publication No. 2015-134157 has disclosed an optical brain-function measuring device that measures a brain function utilizing the NIRS. The device includes a light source that generates an infrared ray, a light detector that detects an infrared ray from a human body, and an optical system that controls an irradiation position of light to a human body. It is disclosed that with this configuration, it is possible to measure a brain function at any position of a human head.

Japanese Unexamined Patent Application Publication No. 2009-136495 has disclosed an environmental control system that appropriately controls the ambient environment of a subject by obtaining data on brain activity at a plurality of measurement sections on the cerebral surface of the subject.

SUMMARY

In one general aspect, the techniques disclosed here feature a biological information measuring device including: a light source that, in operation, emits irradiation light for irradiating a test portion of a subject; a light detector that, in operation, detects light from the subject and outputs an electrical signal corresponding to the light; and a control circuit that, in operation, determines a power of the irradiation light emitted by the light source, and that, in operation, measures biological information related to a blood flow at the test portion based on the electrical signal. The control circuit, in operation, detects a distance between the light source and the test portion based on the electrical signal, and determines the power of the irradiation light such that the power of the irradiation light is increased as the distance increases.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1A:
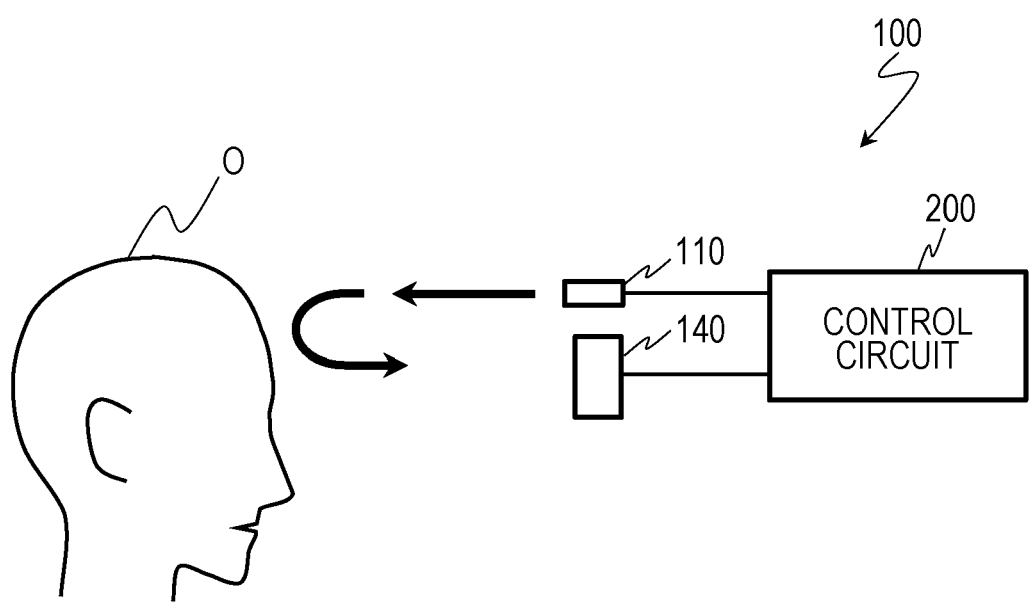
FIG. 1A is a diagram schematically illustrating a general configuration of a biological information measuring device in a first embodiment.

The underlying knowledge forming the basis of the present disclosure will be described before a description of an embodiment of the present disclosure is given.

The inventor of the present application is studying a method including detecting biological information (for instance, information on cerebral blood flow) on the blood of a subject, estimating a level of concentration, emotions and others of the subject, and controlling various instruments based on a result of the estimation. For instance, in application for education using a tablet terminal, the inventor is studying a control method that changes contents of display according to a level of concentration of a learner. Alternatively, in communication (referred to as conversation) of a user with an interactive robot via voice or image, the inventor is studying a control method that changes the contents of the conversation according to a level of concentration or a mental state of the user. In addition, control on an autonomous car according to a level of concentration of a driver, and control on setting the temperature of an air conditioner or changing the sound volume of an audio equipment according to an emotion (including sensation of heat, cold, etc.) of an indoor user are also being studied.

In order to achieve such interactive operations, it is desirable that biological information such as a cerebral blood flow of a user (hereinafter also referred to as a "subject") be appropriately obtained. However, the subject is not still all the time, and usually often moves. When a test portion (for instance, the forehead) of the subject moves, it is difficult to appropriately obtain biological information.

The device in each of Japanese Unexamined Patent Application Publication Nos. 2003-337102 and 2009-136495 assumes a state where the head is still, thus cannot be applied to the application described above.

In the measuring device of Japanese Unexamined Patent Application Publication No. 2015-134157, the power of the light source is uniform all the times irrespective of the distance between a subject and a light detector. Therefore, the power of reflected light and scattered light from the subject decays as the light detector is spaced away from the subject. Consequently, the SN ratio of the measuring device decreases, and the accuracy of detection of biological information is reduced.

Based on the discussion above, the inventor of the present application has devised a novel biological information measuring technique disclosed below.

A non-restricting and exemplary embodiment in the present application provides a technique that enables measurement of biological information even when a subject moves.

The present disclosure includes a biological information measuring device, a biological information measuring module, an integrated circuit, a method for measuring biological information, a computer program, an electronic device, a robot, a vehicle and an environmental control device which are described in the following items.

[Item 1]

A biological information measuring device according to Item1 of the present disclosure includes a light source that, in operation, emits irradiation light for irradiating a test portion of a subject, a light detector that, in operation, detects light from the subject and outputs an electrical signal corresponding to the light, and a control circuit that, in operation, determines a power of the irradiation light emitted by the light source, and that, in operation, measures biological information related to a blood flow at the test portion based on the electrical signal, in which the control circuit, in operation, detects a distance between the light source and the test portion based on the electrical signal, and determines the power of the irradiation light such that the power of the irradiation light is increased as the distance increases.

[Item 2]

In the biological information measuring device according to Item1 of the present disclosure, in operation, the control circuit may further compare a first distance that is the distance at a first time with a second distance that is the distance at a second time after the first time, and when it is determined that the distance has changed as a result of the comparison, the control circuit may determine the power of the irradiation light again.

[Item 3]

In the biological information measuring device according to Item2 of the present disclosure, the light detector may be an image sensor that, in operation, obtains a moving image of the test portion, the moving image including a plurality of frames, and the control circuit may, in operation, make the comparison between the first distance and the second distance for every predetermined number of frames in the plurality of frames.

[Item 4]

In the biological information measuring device according to Item2 of the present disclosure, in operation, the control circuit may further determine whether or not the measuring of the biological information is normal, and when it is detected that the measuring is not normal, the control circuit may make the comparison between the first distance and the second distance.

[Item 5]

In the biological information measuring device according to Item1 of the present disclosure, the light detector may be an image sensor that, in operation, obtains an image of the test portion, the electrical signal may include a signal representing the image, and based on the signal representing the image, the control circuit may, in operation, detect a first brightness that is a brightness of the test portion at a first time, a second brightness that is a brightness of the test portion at a second time after the first time, and a brightness variation amount which is a difference between the first brightness and the second brightness, and the control circuit may, in operation, adjust the power of the irradiation light based on the brightness variation amount.

[Item 6]

In the biological information measuring device according to Item5 of the present disclosure, the image may be a moving image including a plurality of frames, and the control circuit may, in operation, detect the brightness variation amount for every predetermined number of frames in the plurality of frames.

[Item 7]

In the biological information measuring device according to Item5 of the present disclosure, in operation, the control circuit may further determine whether or not the measuring of the biological information is normal, and when it is detected that the measuring is not normal, the control circuit may detect the brightness variation amount.

[Item 8]

In the biological information measuring device according to Item1 of the present disclosure, in operation, the control circuit may further detect a distance variation amount which is a difference between a first distance that is the distance at a first time and a second distance that is the distance at a second time after the first time, and the control circuit may adjust the power of the irradiation light based on the distance variation amount.

[Item 9]

In the biological information measuring device according to Item8 of the present disclosure, the image may be a moving image including a plurality of frames, and the control circuit may, in operation, detect the distance variation amount for every predetermined number of frames in the plurality of frames.

[Item 10]

In the biological information measuring device according to Item8 of the present disclosure, in operation, the control circuit may further determine whether or not the measuring of the biological information is normal, and when it is detected that the measuring is not normal, the control circuit may detect the distance variation amount.

[Item 11]

In the biological information measuring device according to Item1 of the present disclosure, in operation, the control circuit may further detect a position of the test portion based on the electrical signal, and determine an irradiation position of the irradiation light in the subject based on the position of the test portion.

[Item 12]

In the biological information measuring device according to Item11 of the present disclosure, the light detector may be an image sensor that, in operation, obtains an image of the test portion, the electrical signal may include a signal representing the image, and the control circuit may, in operation, detect a position of the test portion by image recognition based on the signal representing the image.

[Item 13]

In the biological information measuring device according to Item1 of the present disclosure, a first light detector and a second light detector may be provided in the biological information measuring device, each of the first light detector and the second light detector being the light detector, the second light detector may be an image sensor, the first light detector may, in operation, detect a first component which is a component of a wavelength included in the irradiation light out of the light from the subject, and output a first electrical signal corresponding to the first component, the second light detector may, in operation, detect a second component which is a component of visible light out of the light from the subject, and output a second electrical signal corresponding to the second component, and the control circuit may, in operation, detect the distance based on the second electrical signal, and measure the biological information based on the first electrical signal.

[Item 14]

In the biological information measuring device according to Item1 of the present disclosure, the irradiation light may be a pulsed light, and the control circuit may, in operation, detect the distance based on a time from when the light source emits the pulsed light to when the light detector detects the pulsed light.

[Item 15]

In the biological information measuring device according to Item11 of the present disclosure, the biological information measuring device may further include an optical element that is disposed on a path of the irradiation light and that, in operation, changes the irradiation position, in which the control circuit may, in operation, control the optical element based on the electrical signal.

[Item 16]

In the biological information measuring device according to Item1 of the present disclosure, the test portion may be a forehead of the subject, and the biological information may be information related to a cerebral blood flow.

[Item 17]

In the biological information measuring device according to Item1 of the present disclosure, the biological information measuring device may further include an interface that, in operation, transmits the electrical signal outputted from the light detector to an external device.

[Item 18]

A the biological information measuring device according to Item 18 of the present disclosure includes a light source that, in operation, emits irradiation light for irradiating a test portion of a subject, a light detector that, in operation, detects light from the subject and outputs a first electrical signal corresponding to the light, a control circuit that, in operation, determines a power of the irradiation light emitted by the light source, and measures biological information related to a blood flow at the test portion based on the first electrical signal, and an interface that, in operation, communicates with an external device including an image sensor that, in operation, obtains an image of the test portion and outputs a second electrical signal including a signal representing the image, in which, in operation, the interface receives the second electrical signal from the external device, and transmits the first electrical signal to the external device, and the control circuit detects a distance between the light source and the test portion based on the second electrical signal, and determines the power of the irradiation light such that the power of the irradiation light is increased as the distance increases.

In the present disclosure, all or a part of any of circuit, unit, device, part or portion, or any of functional blocks in the block diagrams may be implemented as one or more of electronic circuits including, but not limited to, a semiconductor device, a semiconductor integrated circuit (IC) or an LSI. The LSI or IC can be integrated into one chip, or also can be a combination of plural chips. For example, functional blocks other than a memory may be integrated into one chip. The name used here is LSI or IC, but it may also be called system LSI, VLSI (very large scale integration), or ULSI (ultra large scale integration) depending on the degree of integration. A Field Programmable Gate Array (FPGA) that can be programmed after manufacturing an LSI or a reconfigurable logic device that allows reconfiguration of the connection or setup of circuit cells inside the LSI can be used for the same purpose.

Further, it is also possible that all or a part of the functions or operations of the circuit, unit, device, part or portion are implemented by executing software. In such a case, the software is recorded on one or more non-transitory recording media such as a ROM, an optical disk or a hard disk drive, and when the software is executed by a processor, the software causes the processor together with peripheral devices to execute the functions specified in the software. A system or apparatus may include such one or more non-transitory recording media on which the software is recorded and a processor together with necessary hardware devices such as an interface.

Hereinafter, an embodiment of the present disclosure will be described in detail with reference to the drawings. It should be noted that each of the embodiments described below provides a general or specific example. Numerical values, shapes, materials, structural components, the arrangement and connection of the structural components, steps, the sequence of the steps presented in the following embodiments are mere examples, and are not intended to limit the scope of the present disclosure. Various aspects described in the present description may be combined with each other as long as no contradiction occurs. Also, among the structural components in the subsequent embodiment, components not recited in any one of the independent claims which indicate the broadest concepts are described as arbitrary structural components. In the following description, structural components having substantially the same function or similar functions are labeled with a reference symbol in common, and a description may be omitted.

First Embodiment

First, a biological information measuring device in a first embodiment will be described. The biological information measuring device measures the cerebral blood flow of a tested section of a subject in a non-contact manner.

FIG. 1A is a diagram schematically illustrating a general configuration of a biological information measuring device 100 in the first embodiment.

The biological information measuring device 100 includes a light source 110, a light detector 140, and a control circuit 200 connected to the light source 110 and the light detector 140. The light emitted from the light source 110 is reflected by a test portion (the forehead in the illustrated example) of the subject O, and enters the light detector 140. The light detector 140 converts the entered light into an electrical signal, and outputs the signal. The control circuit 200 adjusts the position and power of the light irradiated by the light source 110, based on the signal outputted from the light detector 140. To put it simply, the control circuit 200 performs the following operations:

(1) The position of and distance to a test portion are identified based on an electrical signal (for instance, a signal representing an image) outputted from the light detector 140 during emission of the light source 110.

(2) The position, in the subject O, irradiated with light and the power of light are determined based on the identified position and distance of the test portion. For instance, an optical element such as a micro electro mechanical systems (MEMS) mirror (not illustrated) is controlled so that the position of the test portion is properly irradiated with light. The light source 110 is caused to emit light such that the power of the light reaching the light detector 140 becomes substantially a predetermined value. For instance, the power of the light emitted by the light source 110 is increased as the distance to a test portion increases, and the power of the light emitted by the light source 110 is decreased as the distance decreases.

Here, a method for adjusting the power of light will be described. The power of light is defined by the energy of light per unit time, and the unit is watt (W)=Joule/second (J/S).

When irradiation light is continuous light, light power is controllable by controlling the intensity of the irradiation light. Specifically, the light power can be increased by enhancing the intensity of the irradiation light. Also, the light power can be decreased by reducing the intensity of the irradiation light.

When an irradiation time of continuous light is shorter than the unit time, the light power can be controlled further by control of the irradiation time. The unit time may be 1 second, for instance. The light power can be increased by increasing the irradiation time.

When the irradiation light is a pulsed light, it is possible to control the light power by controlling the intensity of the irradiation light, and further controlling the duty ratio (ratio of the irradiation time to the period of the pulse) of the pulse. The light power can be increased by enhancing the intensity of the irradiation light. The light power can be increased by increasing the duty ratio of the pulse. Also, the light power can be decreased by reducing the intensity of the irradiation light.

Furthermore, when the irradiation time of a group of pulsed beams is shorter than the unit time, the light power is controllable by controlling the number of pulses. In this process, the light power can be enhanced by increasing the number of pulses. Also, the light power can be reduced by decreasing the number of pulses.

The control circuit 200 first performs the above-described operations when starting to detect biological information (at the time of initial operations). With this, a test portion is irradiated with light having appropriate power, and thus biological information can be detected with high accuracy. However, with the unchanged state, it is not possible to continue detection when the subject O moves. Thus, the control circuit 200 in the embodiment performs the above-described operations for every predetermined time while detecting biological information. In this manner, even when the subject O moves, the direction and power of light are maintained appropriately, and it is possible to continue detection of biological information.

The above-described operations may be performed at least one timing of the time of initial operations and during the detection, without being limited to the configuration in which the above-described operations are performed both at the time of initial operations and during the detection. Thus, at least one timing of the time of initial operations and during the detection, highly accurate detection of biological information is possible irrespective of the position of a test portion of the subject O.

Hereinafter, the configuration and operation of this embodiment will be described in detail.

[Configuration of Biological Information Measuring Device 100]

Figure 1B:
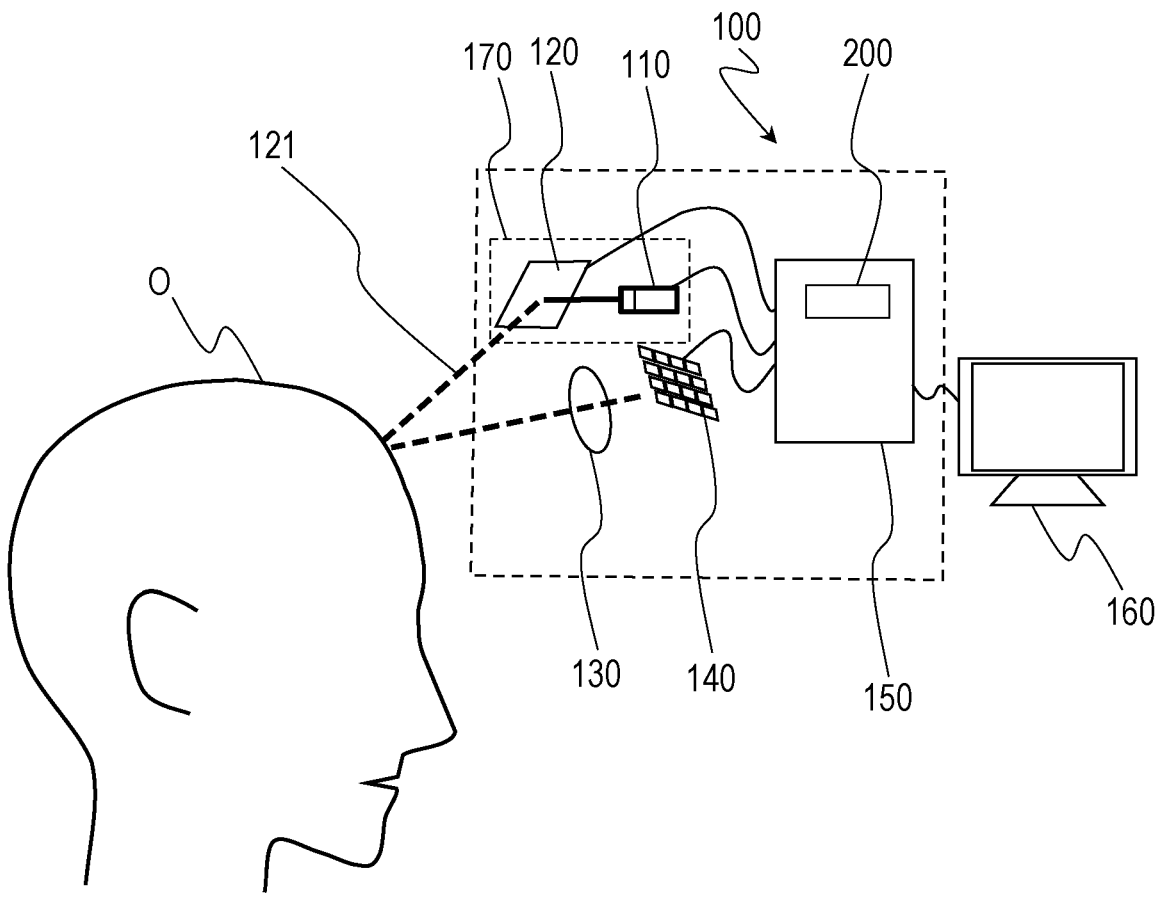
FIG. 1B is a diagram illustrating a more detailed configuration example of the biological information measuring device in this embodiment.

FIG. 1B is a diagram illustrating a more detailed configuration example of the biological information measuring device 100 in this embodiment. In addition to the above-described light source 110, light detector 140, control circuit 200, the biological information measuring device 100 in the example includes an optical element 120 that changes the path of the light emitted from the light source 110, an optical system 130 that collects the light from the subject O, and a processor 150 that processes a signal outputted from the light detector 140, and controls the light source 110, and the optical element 120. The control circuit 200 is provided inside the processor 150. FIG. 1B also illustrates a display (display device) 160 which is an external component of the biological information measuring device 100. The display 160 is connected to the control circuit 200, and displays a processing result.

Hereinafter, the detail of each component will be described.

The light source 110 irradiates a test portion of the subject O with light. The test portion in this embodiment is the forehead of the subject O. The forehead is irradiated with light, and reflection light or scattered light is detected, thereby making it possible to obtain information on cerebral blood flow. The "scattered light" includes reflected scattered light and transmitted scattered light. In the following description, reflected scattered light may be simply referred to as "reflected light". When information on blood other than the cerebral blood flow is obtained, a part other than the forehead (for instance, an arm or a leg) may be a test portion. In the following description, the test portion is the forehead unless otherwise stated particularly. In the following description, the subject O is assumed to be a human. However, the subject O may be other than a human, specifically an animal having a skin and part of the skin, in which no hair is grown. The term "subject" in the present description indicates a general subject including such an animal.

The light source 110 emits light with a wavelength of 650 nm or greater and 950 nm or less, for instance. This wavelength range is included in a wavelength range from red to the near-infrared. The aforementioned wavelength range is called "biological window", and it is known that the rate of absorption of light in the wavelength range within the body is low. Although the light source 110 in this embodiment will be described as a component that emits light in the aforementioned wavelength range, light in another wavelength range may be used. In the present description, the term "light" is used for not only visible light but also infrared rays.

Figure 2:
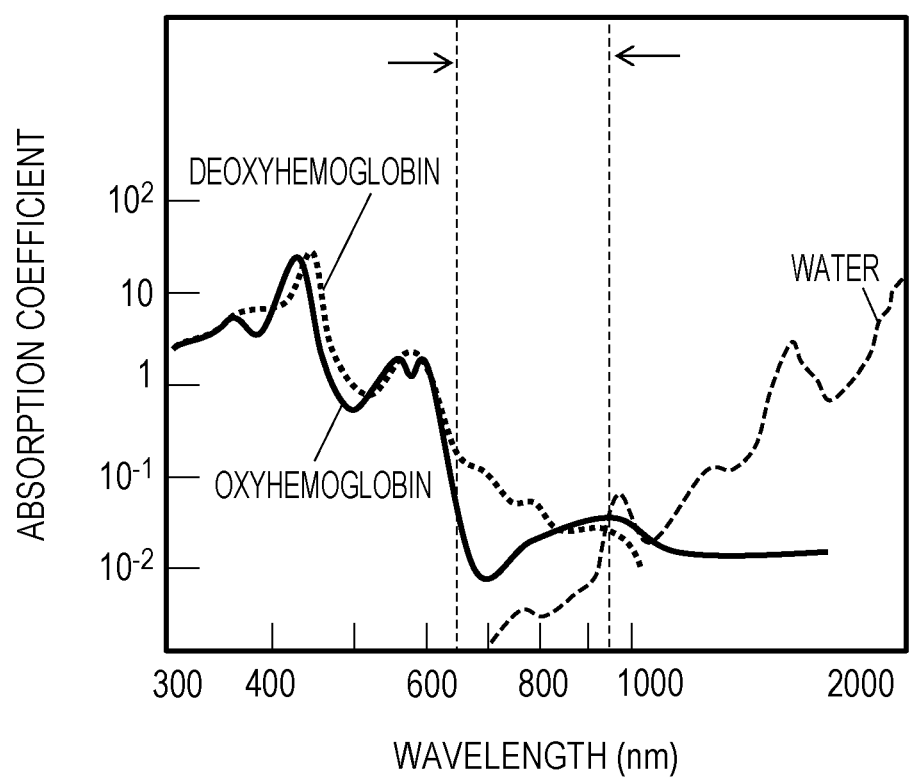
FIG. 2 is a graph illustrating a wavelength dependence of light absorption coefficient of each of oxyhemoglobin, deoxyhemoglobin, and water.

FIG. 2 is a graph illustrating a wavelength dependence of light absorption coefficient of each of oxyhemoglobin, deoxyhemoglobin, and water. In the visible light range with 650 nm or less, light absorption by the hemoglobin ($HbO_2$ and Hb) in blood is high, whereas in the wavelength range with 950 nm or greater, light absorption by water is high. On the other hand, in the wavelength range of 650 nm or greater and 950 nm or less, the absorption coefficients of hemoglobin and water are relatively low, and the scattering coefficients are relatively high. Therefore, light in the wavelength range, after entering the inside of a body, is severely scattered and returned to the body surface. Consequently, information on the inside of a body can be efficiently obtained. Thus, in this embodiment, the light in the aforementioned wavelength range is mainly used.

The light source 110 may be a laser light source such as a laser diode (LD) that continuously emits pulsed light, for instance. When the subject O is a human as in this embodiment, it is desired that the effect of emitted light on the retina be taken into consideration. When a laser light source is used as the light source 110, the light source 110 may be set so as to satisfy laser safety standard Class 1 which is formulated in each country. When Class 1 is satisfied, the subject O is irradiated with low illumination light with accessible emission limit, AEL less than 1 mW. However, the light source 110 itself may not satisfy Class 1. For instance, the laser safety standard Class 1 may be satisfied by diffusing or attenuating light using an element such as a diffuser plate or an ND filter disposed between the light source 110 and the subject O.

The light source 110 is not limited to a laser light source and may be another type of light source such as a light emitting diode (LED). As the light source 110, for instance, a semiconductor laser, a solid-state laser, a fiber laser, a superluminescent diode, or an LED may be widely used. The entire device can be miniaturized by combining one of these and a small-sized optical element 120. The light source 110 is not limited to a light source that emits pulsed light, and may be a light source that emits continuous light.

The light source 110 starts or stops light-emission, and changes the power of light-emission according to a command from the control circuit 200. Light 121 emitted from the light source 110 is used to detect information on cerebral blood flow, and the position of and distance to the forehead.

The optical element 120 is disposed on an optical path of the light 121, between the light source 110 and a test portion (specifically, the forehead) of the subject O. The optical element 120 changes the optical path of the light 121 to guide the optical path to the forehead. In response to a command from the control circuit 200, the optical element 120 adjusts the irradiation position of the light 121 on the forehead. When the optical element 120 includes a mirror, the irradiation position of the light 121 on the forehead is changeable by changing the angle of the mirror.

The optical element 120 may be, for instance, a MEMS mirror. Use of particularly a dual-axis scanning mirror enables two dimensional adjustment of the irradiation position of light at a test portion. This enables compact and quick adjustment of an irradiation position of light. In addition, as the optical element 120, for instance, a polygon mirror, a galvano mirror, or a rotational prism may be used.

In the present description, the combination of the light source 110 and the optical element 120 may be referred to as the "light source unit". A light source unit 170 including the light source 110 and the optical element 120 may be formed as an optical module, for instance. In the present description, an emission direction of light from the light source unit 170 may be expressed as an "emission direction of light from the light source".

Figure 1C:
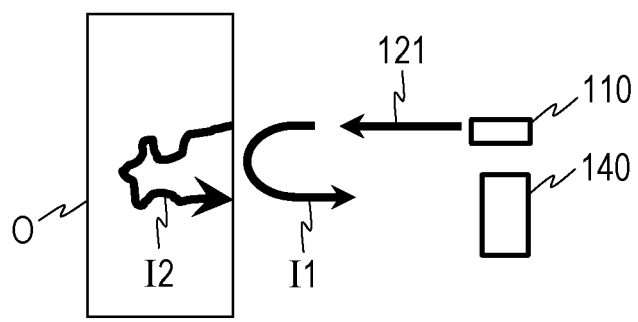
FIG. 1C is a diagram illustrating an example of light reflected and scattered by a subject which is irradiated with light.

FIG. 1C is a diagram schematically illustrating the manner in which the light (which is referred to as "return light") reflected and scattered by subject O irradiated with the light 121 reaches the light detector 140. The return light from the subject O includes a component reflected by the surface of the subject O (surface reflection component 11), a component (internal scattering component 12) which is reflected (including diffusely reflected) once inside the subject O, scattered, or multiply scattered. Between these, a component desired to be detected is the internal scattering component 12. However, in general, the signal strength of the internal scattering component 12 is low. This is because, as described above, in addition to irradiation with an extremely small quantity of light satisfying the laser safety standard, scattering and absorption of light by the scalp, cerebral fluid, skull bone, gray matter, white matter, and blood flow is high. Furthermore, change in signal strength, which is caused by a change in blood flow rate or blood flow component when the brain is active, corresponds to one-several tenths of the aforementioned signal strength, and is extremely small. Thus, detection may be made without allowing the presence of the surface reflection component 11 as much as possible, the surface reflection component 11 being equivalent to several thousand to several ten thousand times a signal component to be detected. Thus, the light detector 140 may be formed of an image sensor having the function of an electronic shutter, and the control circuit 200 may appropriately control shutter timing, thereby detecting the internal scattering component 12 only. Such a configuration is disclosed, for instance, in the description of Japanese Patent Application No. 2015-122390. The entire disclosure of Japanese Patent Application No. 2015-122390 is incorporated in the present application.

The optical system 130 focuses the light 121 reflected or scattered by a test portion to the light detector 140. The optical system 130 is, for instance, a single or multiple lens, and may include a mirror. When the optical system 130 includes a lens, the light-receiving surface and light-emitting surface of the lens may be each provided with an antireflective coating that reduces reflection of the light 121. This enables detection of information on cerebral blood flow with higher sensitivity.

The light detector 140 detects return light from the subject O. The light detector 140 includes a plurality of light detection elements arranged one-dimensionally or two-dimensionally. Each of the light detection elements includes, for instance, a photodiode, and outputs an electrical signal according to the power (light quantity) of the light 121 from a test portion. The light detection element may be another element such as a photomultiplier tube (PMT). Using a highly sensitive avalanche photodiode or photomultiplier tube as a light detection element makes it possible to obtain information on cerebral blood flow with higher sensitivity.

The light detector 140 may be an image sensor such as a CCD or a CMOS having sensitivity to light in a wavelength range including the wavelength of the light emitted from the light source 110. Using an image sensor makes it possible to obtain a two-dimensional intensity distribution (for instance, moving images) of light. As described later, by utilizing the obtained moving images, a characteristic pattern of the test portion can be extracted by image recognition to identify the position of the test portion in the image. Alternatively, movement of the test portion may be detected by movement detection.

The light detector 140 also has a configuration that allows measurement of the distance to the subject O. For instance, the distance to the subject O can be measured using a time-of-flight (TOF) technique. In the TOF technique, a time taken for irradiation light to reach the light detector 140 after reflected by the subject O, in short, a time of flight is measured. The distance to the test portion in the subject O can be measured based on the difference between the phase of light detected by each detection element and the phase of light in the light source 110.

It is to be noted that the optical system 130 and the light detector 140 may be integrally formed. In addition, the light source unit 170, the optical system 130, and the light detector 140 may be integrally formed. In this manner, a portable small-sized optical unit is provided. A small-sized optical unit may be connected to the processor 150 by a cable such as a USB cable.

Figure 3:
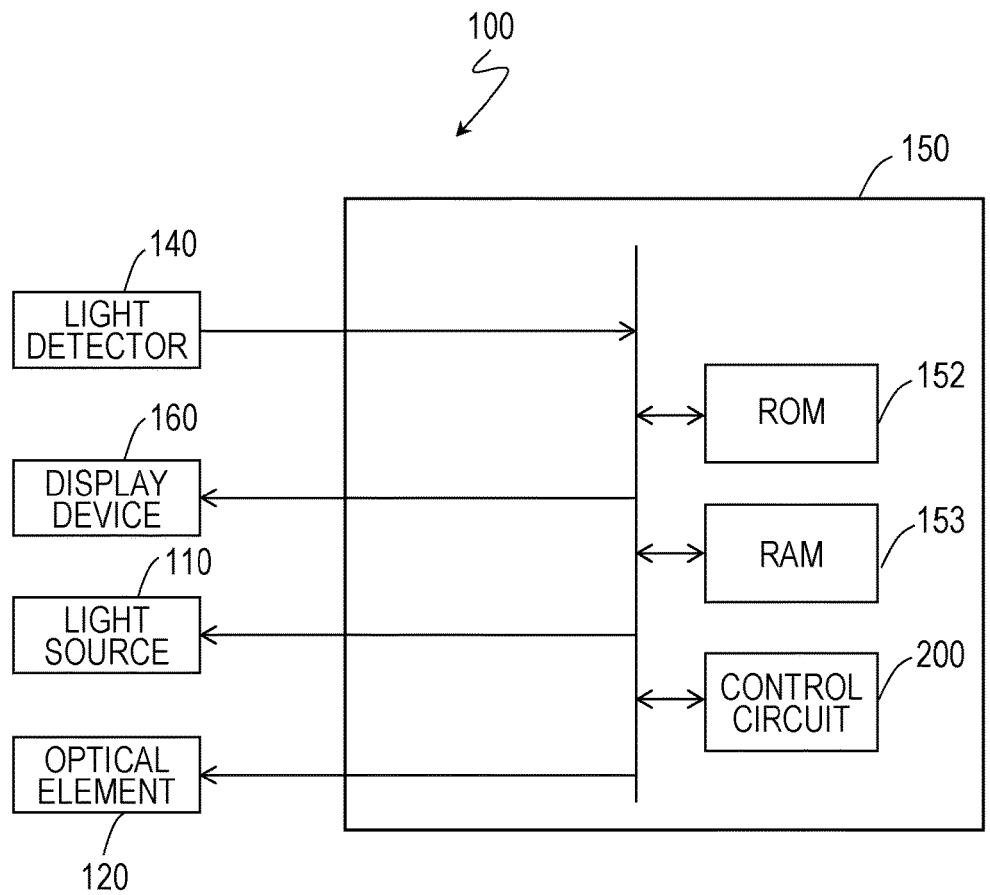
FIG. 3 is a diagram illustrating the internal configuration of a processor.

FIG. 3 is a diagram illustrating the internal configuration of the processor 150.

The processor 150 is connected to the light source 110, the optical element 120, the light detector 140, and the display 160, and controls these components. The processor 150 includes a read only memory (ROM) 152, a random access memory (RAM) 153, and the control circuit 200. The control circuit 200 is an integrated circuit including, for instance, a central processing unit (CPU). The control circuit 200 controls the operation of the biological information measuring device 100. The ROM 152 stores computer programs to be executed by the control circuit 200. Each of the computer programs is a group of commands that cause the control circuit 200 to execute, for instance, the processing or part of the processing illustrated by the later-described flowchart. Such a computer program is downloadable, for instance, via a network, and may be stored in a computer-readable recording medium. The RAM 153 is a work memory for loading a program which is to be executed by the control circuit 200. The RAM 153 is also a storage device that stores a signal (data) outputted from the light detector 140 and data on measured biological information. In the present description, "biological information" indicates various information on blood, such as a heart rate, a blood flow rate, a blood pressure, an oxygen saturation in blood. In particular, in this embodiment, the aforementioned information on cerebral blood flow is measured by the control circuit 200. With this, a level of concentration and a state of feelings of the subject O can be estimated.

The processor 150 may be a general-purpose computer such as a personal computer or a tablet computer. Such a computer includes a CPU that controls the entire operation of the processor 150. The CPU may execute part or all of the operation to be performed by the control circuit in the present disclosure. In that case, the CPU of the general-purpose computer functions as at least part of the "control circuit" in the present disclosure.

The light source 110, the optical element 120, and the light detector 140 are connectable to the processor 150 via various interfaces. For instance, when the light detector 140 is an image sensor, those components are connectable to the processor 150 utilizing a terminal in accordance with the MIPI standard (registered trademark). Also, the light source 110 and the optical element 120 are connectable to the processor 150 utilizing a USB interface, for instance.

As illustrated, the processor 150 connectable to the display 160 that displays moving images and biological information of a subject. The display 160 is a liquid crystal or organic EL display, for instance. The display 160 is connectable to the processor 150 utilizing a terminal in accordance with the HDMI (registered trademark) standard, for instance. A user of the biological information measuring device 100 can obtain various information on biological activity from the display 160.

It is also possible to transmit and/or receive data by wireless communication other than the above-described connection via a cable. It is possible to utilize communication in accordance with the Wi-Fi (registered trademark) standard or the ZigBee (registered trademark) standard, for instance.

The biological information measuring device 100 can measure a two-dimensional intensity distribution of light, and to measure various biological information such as a blood flow rate, a blood pressure, an oxygen saturation in blood, and a heart rate in the brain based on the intensity distribution. Such a measurement technique is disclosed by Japanese Unexamined Patent Application Publication No. 2015-134157, and can be utilized in the present disclosure. The entire disclosure of Japanese Unexamined Patent Application Publication No. 2015-134157 is incorporated by reference in the present application.

It is known that there is a close relationship between a change in cerebral blood flow rate or blood flow component (for instance, hemoglobin) and neural activity of human. For instance, in response to a change in feelings of human, the activity of nerve cells changes, and thereby the cerebral blood flow rate or blood flow component is changed. Therefore, measurement of biological information such as a change in the cerebral blood flow rate or blood flow component makes it possible to estimate the mental state of a subject. The mental state of a subject indicates, for instance, a feeling (such as comfort, discomfort), an emotion (such as relief, anxiety, sadness, anger), a physical condition (such as liveliness, fatigue), and temperature sensation (such as hot, cold, sultry). In addition, as a derivative state, the mental state also includes an index indicating a degree of brain activity, for instance, a level of proficiency, a level of mastery, and a level of concentration.

[1-2. Operation of Biological Information Measuring Device]

Figure 4:
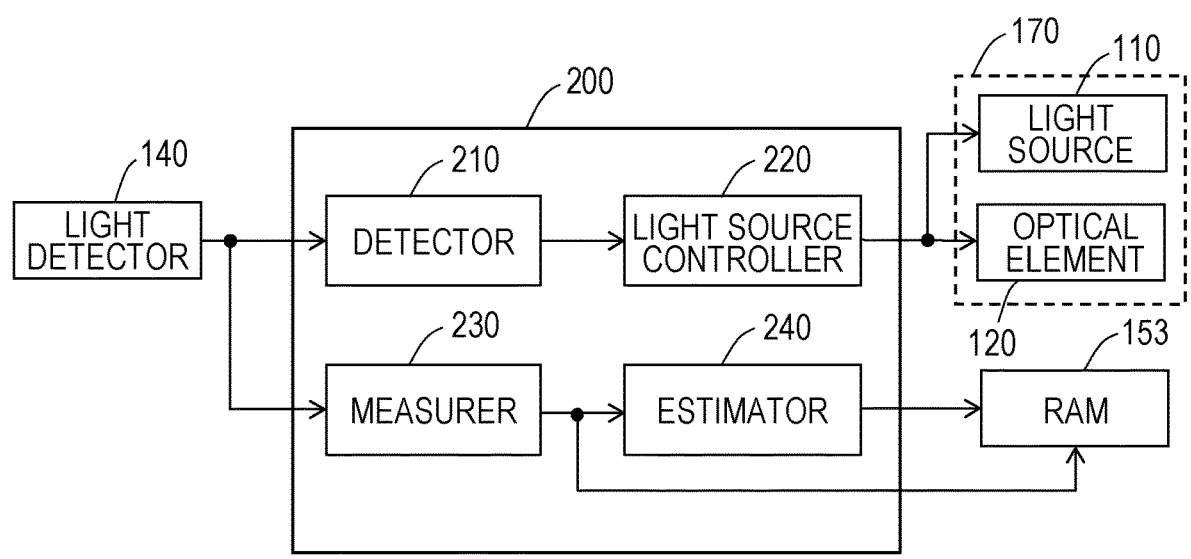
FIG. 4 is a diagram schematically illustrating typical functional blocks of a control circuit.

FIG. 4 is a diagram schematically illustrating typical functional blocks of the control circuit 200. The control circuit 200 has a detector 210, a light source controller 220, a measurer 230, and an estimator 240. The control circuit 200 is an integrated circuit such as an application specific integrated circuit (ASIC) or a field-programmable gate array (FPGA). The function corresponding to each functional block may be mounted in the control circuit 200 by either one of software and hardware. For instance, an internal ROM (not illustrated) of the control circuit 200 or a computer program stored in the ROM 152 may include a command group for executing the function corresponding to each functional block. The control circuit 200 is a product which could be distributed in the market as a single unit.

Figure 5:
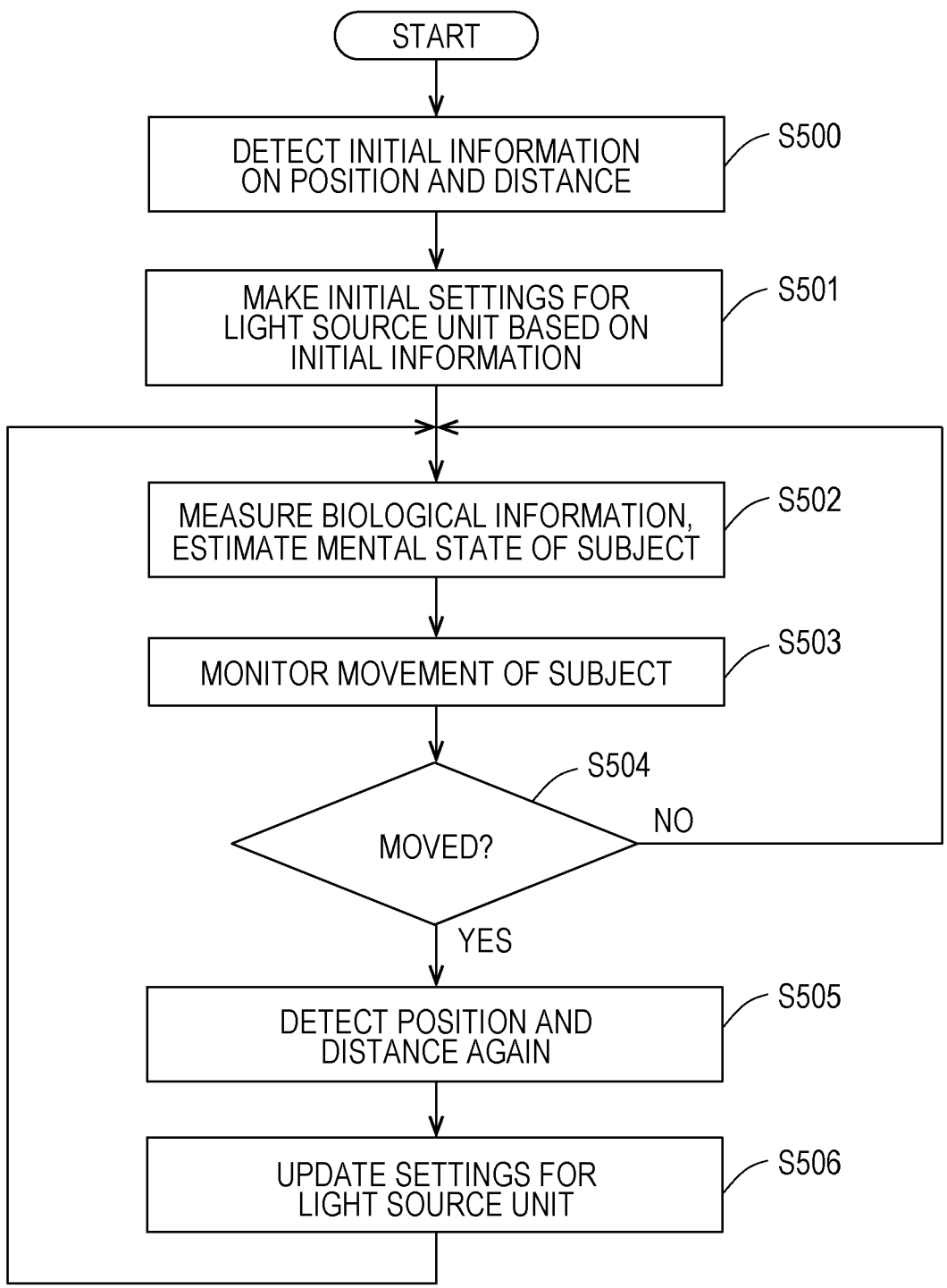
FIG. 5 is a flowchart illustrating an example of processing of the biological information measuring device.

FIG. 5 is a flowchart illustrating an example of processing of the biological information measuring device 100. Hereinafter, a description is given under the assumption that the operations are predominantly performed by the control circuit 200 which executes the function corresponding to each functional block. As described above, when a CPU is provided independently from the control circuit 200, the CPU may execute part of the function of the control circuit 200. Hereinafter, a description is given under the assumption that the light detector 140 is a TOF image sensor and the optical element 120 is a MEMS mirror.

(Step S500)

The detector 210 of the control circuit 200 detects the position of the forehead of the subject O and the distance between the light source 110 and the forehead. Specifically, the detector 210 utilizes moving images including a plurality of frame images outputted from the light detector 140, and obtains the position information on the forehead in the frame images by image recognition. For instance, the position of the forehead is identified by pattern matching that uses templates associated with a human forehead. The position information may be information that indicates, for instance, the central position of an image in a detected pattern. The templates are pre-stored in the ROM 152, for instance. A wide variety of publicly known techniques may be used for the image recognition without being limited to a specific technique. Also, the detector 210 calculates (ranges) the distance to the subject O based on a signal including information that indicates a phase difference of the power of the light outputted from the light detector 140.

The light source controller 220 of the control circuit 200 controls the light source 110 and the optical element 120 (in other words, the light source unit 170).

The light source controller 220 and the detector 210 perform the above-described operation as an initial operation of the biological information measuring device 100. Specifically, at the start of measurement of biological information using the biological information measuring device 100, the light source controller 220 commands the light source unit 170 to emit light. The power and emission direction of light at this point are set to predetermined initial values. The detector 210 performs the initial operation and obtains initial information indicating the position of and distance to a test portion. The initial operation corresponds to calibration of the biological information measuring device 100.

(Step S501)

The light source controller 220 sets the initial values of the emission direction of light and the light power based on the initial information from the detector 210. Specifically, the initial value of the emission direction of light is set to the optical element 120. The optical element 120 sets, for instance, the angle of MEMS mirror to an angle according to the initial value, and determines an irradiation position of the light 121 on the forehead. The initial value of light power is set to the light source 110. The light source 110 emits a light 121 to the subject O, the light 121 having a power according to the initial value. The above operations allow light having appropriate power to be emitted in an appropriate direction according to the position of the subject O facing the biological information measuring device 100.

(Step S502)

The measurer 230 of the control circuit 200 measures biological information on the subject O based on an output signal from the light detector 140. For instance, the measurer 230 utilizes the NIRS to measure the oxyhemoglobin concentration and deoxyhemoglobin concentration in the blood in the brain as biological information. The estimator 240 of the control circuit 200 estimates the mental state of the subject based on the measured biological information. For instance, the estimator 240 estimates a mental state such as a level of concentration, an emotion of the subject O based on the oxygenation state of hemoglobin.

Here, a specific example of a method for measuring biological information will be described.

A major role of blood is to receive oxygen from the lungs and carry the oxygen to tissues, and to receive carbon dioxide from the tissues to circulate the carbon dioxide in the lungs. Approximately 15 g of hemoglobin is present in 100 ml of blood. Oxyhemoglobin is hemoglobin combined with oxygen, whereas deoxyhemoglobin is hemoglobin not combined with oxygen. As illustrated in FIG. 2, oxyhemoglobin and deoxyhemoglobin have different light absorption properties. Oxyhemoglobin absorbs infrared rays with a wavelength greater than approximately 830 nm relatively well, and deoxyhemoglobin absorbs red light (for instance, a wavelength of 660 nm) relatively well. The rates of absorption of near-infrared rays with a wavelength of 805 nm are the same for both oxyhemoglobin and deoxyhemoglobin. Thus, in this embodiment, two wavelengths of 660 nm (red light) and 830 nm (infrared light) are used, and the light power from a test portion is measured for each of the wavelengths. Based on the ratio between the powers of these red light and infrared light, the ratio (oxygen saturation) of the concentrations of the two types of hemoglobin can be determined. As a combination of two wavelengths to be used, a wavelength shorter than 805 nm and a wavelength longer than 805 nm may be combined. The oxygen saturation is a value that indicates the percentage of hemoglobin combined with oxygen out of the hemoglobin in blood. The oxygen saturation is defined by the following expression, where C(Hb) is the concentration of deoxyhemoglobin, and C(HbO$_2$) is the concentration of oxyhemoglobin.

$$\text{Oxygen saturation} = C(HbO_2)/[C(HbO_2)+C(Hb)] \times 100 \, (\%)$$

A human body contains, other than the blood, a component that absorbs light with a wavelength of red to near-infrared rays, and a temporal variation of rate of absorption of light is mainly caused by the hemoglobin in arterial blood.

Thus, an oxygen saturation in blood can be measured with high accuracy based on the variation of rate of absorption. The arterial blood pumped from the heart flows through the blood vessels as pulse waves. On the other hand, the venous blood has no pulse wave. Light, with which a living body is irradiated, passes through the living body while being absorbed by tissues in the living body, such as an artery and vein and tissues other than the blood. The thickness of each tissue other than the arteries has no temporal variation. Thus, scattered light from the inside of a living body exhibits a temporal change in intensity according to a change of the thickness of an arterial blood layer due to pulsation. The change in intensity reflects the change of the thickness of the arterial blood layer, and is free from the effect of the venous blood and the tissues. Thus, the information on arterial blood can be obtained by focusing attention on only varied components of the scattered light. A pulse rate can also be determined by measuring the period of a component that changes with time.

When nerve cells are active, the oxygen carried by the hemoglobin in the blood in the capillary vessels is consumed. It is known that an increase in blood flow occurs associated with local response due to the consumption of oxygen. Also, it is known that the deoxyhemoglobin temporarily increases because of delivery of oxygen to a body tissue by the oxyhemoglobin in the capillary vessels. For instance, it is assumed that the subject O is learning by solving a problem. In this case, the cerebral blood flow rate may change every moment according to a level of concentration. As the level of concentration enhances, the cerebral blood flow rate increases, and the oxygen saturation in blood tends to decrease. Thus, the estimator 240 can determine the level of concentration of the subject O based on, for instance, the amount of change from a reference value of the cerebral blood flow rate or the oxygen saturation in blood. In this embodiment, a table is pre-stored in the ROM 152, that associates a level of concentration with the amount of change from a reference value of the cerebral blood flow rate or the oxygen saturation in blood. The estimator 240 can determine the level of concentration of learning from the measured biological information by referring to the table. A result of measurement by the measurer 230 and a result of estimation by the estimator 240 are temporarily held in the RAM 153, for instance.
(Step S503)

As described above, it is assumed, for instance, that the subject O is learning by solving a problem. In this case, it is presumed that the head of the subject O, specifically, the forehead as a test portion moves during measurement. Thus, the detector 210, after performing the initial operation, monitors whether the subject (particularly the head) has moved. For instance, the detector 210 calculates a motion vector between the consecutive frame images. When the magnitude of the motion vector is greater than or equal to a threshold value, the detector 210 determines that the subject O has moved, and when the magnitude of the motion vector is less than the threshold value, the detector 210 determines that the subject O has not moved. For instance, the threshold value is pre-stored in the ROM 152.

The detector 210 does not need to determine the movement of the subject O successively, and may determine the movement for every predetermined number of frames (for instance, 300 frames). In this manner, the power consumption of the control circuit 200 can be reduced.

When the detector 210 determines that the subject O has not moved, the processing returns to step S502 again. Therefore, the setting of the light source unit 170 remains the initial setting. When the detector 210 determines that the subject O has moved, the processing proceeds to step S505.

It is to be noted that the processing may proceed to step S505, for instance, when measurement of biological information in step S502 is repeatedly performed without monitoring the subject O using such a motion vector and it is detected that normal measurement is no longer possible. Alternatively, the position and distance may be detected simply for every predetermined time (for instance, several seconds to several minutes). Here, whether or not measurement is normal can be determined by measuring the signal level of an electrical signal, which is inputted to the control circuit and corresponding to the blood flow at the test portion. The level of an electrical signal decreases and SN ratio thereof deteriorates as the distance between the light source 110 and the test portion increases. Thus, when the signal level becomes lower than or equal to a predetermined value, the distance between the light source 110 and the test portion is detected again, and the power of light is increased so that the SN ratio falls within a predetermined range.

On the other hand, the electrical signal is saturated, as the distance between the light source 110 and the test portion decreases. Thus, when the signal level becomes higher than a predetermined value, the distance between the light source 110 and the test portion is detected again, and the power of light is decreased so that the signal level is less than or equal to a predetermined value and the SN ratio becomes within a predetermined range.
(Step S505)

The detector 210 again detects the position of the forehead of the subject O, and the distance between the light source 110 and the forehead, and generates updated information on the position and distance.
(Step S506)

The light source controller 220 adjusts the emission direction of light and the light power based on the updated information from the detector 210. Specifically, the updated value of the emission direction of light is set to the optical element 120, and the updated value of the light power is set to the light source 110. The optical element 120 changes the angle of the MEMS mirror to an angle according to the updated value, and changes the irradiation position of the light 121 on the forehead. The light source 110 changes the light power to a light power value indicated by the updated value. When the setting of the light source unit 170 is updated, the processing returns to step S502 again.

With the above operations, the setting of the light source unit is optimized at the time of initial operations and during measurement of biological information. It is to be noted that in this embodiment, the optimization is performed both at the time of initial operations and during the measurement of biological information. The present disclosure, however, is not necessarily limited to such a configuration. The optimization may be performed at least one timing of the time of initial operations and during the measurement of biological information.

[1-3. Modification]

Next, a modification of this embodiment will be described.

Figure 6:
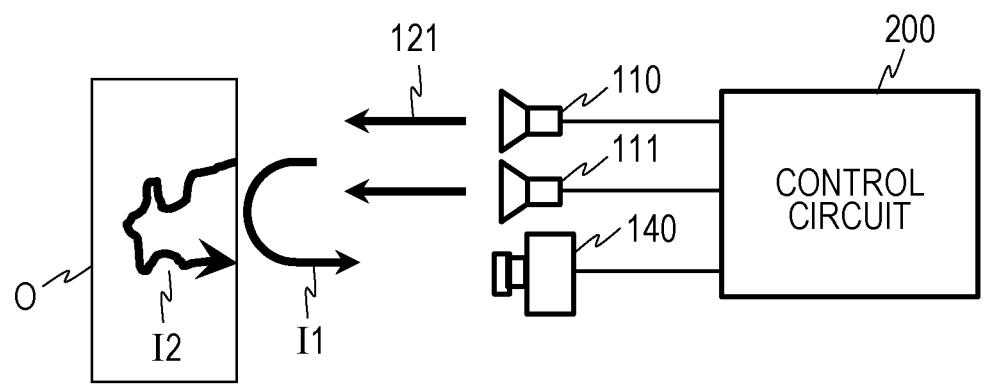
FIG. 6 is a diagram schematically illustrating a modification of the configuration of the light source.

FIG. 6 schematically illustrates a modification of the configuration of the light source. The biological information measuring device in the modification includes two light sources 110, 111. The two light sources 110, 111 are connected to the control circuit 200.

The light sources 110, 111 emit light with different wavelength ranges. The wavelengths of the light emitted by the light sources 110 and 111 may be, for instance, 650 nm and 830 nm mentioned above. However, without being limited to this combination of wavelengths, various combinations may be adopted. In the case where an object to be measured is a body tissue as in this embodiment, when the wavelength is greater than 805 nm, as illustrated in FIG. 2, the absorbance of oxyhemoglobin is higher than the absorbance of deoxyhemoglobin. On the other hand, when the wavelength is less than 805 nm, the opposite property is exhibited. Now, for instance, the light source 110 is assumed to emit light with a wavelength near 750 nm, and the light source 111 is assumed to emit light with a wavelength near 850 nm. In this case, when the light power of each of the internal scattering component 12 due to the light from the light source 110 and the internal scattering component 12 due to the light from the light source 111 is measured, the amounts of change from the initial values of the concentrations of $HbO_2$ and Hb in blood can be determined by solving a predetermined simultaneous equations.

The control circuit 200 calculates, for instance, the amounts of change from the initial values of the concentrations of $HbO_2$ and Hb in blood by solving the simultaneous equations using the light power of each of the internal scattering component 12 due to the light from the light source 110 and the internal scattering component 12 due to the light from the light source 111. Independently from the control circuit 200, a calculation circuit (not illustrated), which solves the simultaneous equations, may be separately provided.

Although the number of light sources is two in the above example, three or more light sources having different wavelength ranges of emission light may be used. Alternatively, a light source having a changeable wavelength range of light may be used. Such a configuration allows more biological information on blood to be obtained.

Figure 7:
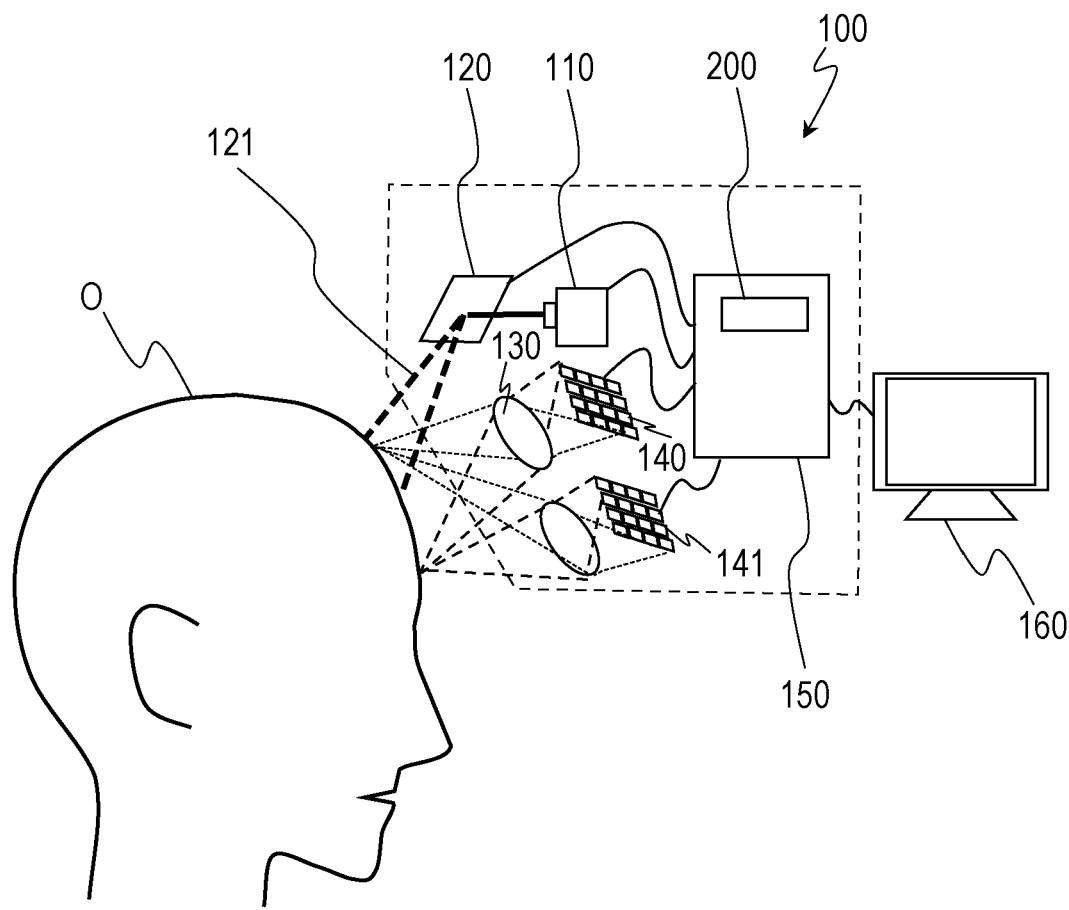
FIG. 7 is a diagram schematically illustrating an configuration example of the biological information measuring device further including an image sensor separately from the light detector.

FIG. 7 is a diagram schematically illustrating a configuration example of the biological information measuring device 100 further including an image sensor 141 separately from the light detector 140. Like this, the biological information measuring device 100 may include another image sensor 141 independent from the light detector 140. With this configuration, the light detector 140 is used as a sensor that specializes in, for instance, biological information measurement, and the position of and distance to a test portion are detected based on the output signal from the image sensor 141. The control circuit 200 may detect movement of the subject using moving images based on the output signal of the image sensor 141. Alternatively, the control circuit 200 may detect the distance based on the output signal of the light detector 140, and may detect the position based on the output signal of the image sensor 141, or the control circuit 200 and the light detector 140 may switch functions. In the present description, the light detector 140 may be referred to as the "first light detector", and the image sensor 141 may be referred to as the "second light detector". Also, an electrical signal outputted from the first light detector may be referred to as a "first electrical signal", and an electrical signal outputted from the second light detector may be referred to as a "second electrical signal".

The biological information measuring device 100 according to this embodiment can measure biological information other than the cerebral blood flow. Some specific examples will be described below.

When the blood flow rate changes, the reflectivity of light changes. Utilizing this, exposed test portions such as the face or hand are irradiated with near-infrared light and reflected light is detected, thereby making it possible to measure a pulse rate and a level of concentration in a non-contact manner. According to the above-described flow illustrated in FIG. 5, the control circuit 200 detects initial information on the position and distance at a test portion, then sets the initial values of the emission direction of light and the light power to the light source unit 170 based on the initial information. Subsequently, the control circuit 200 adjusts the emission direction of light and the light power according to the movement of the test portion while monitoring the movement.

Figure 8:
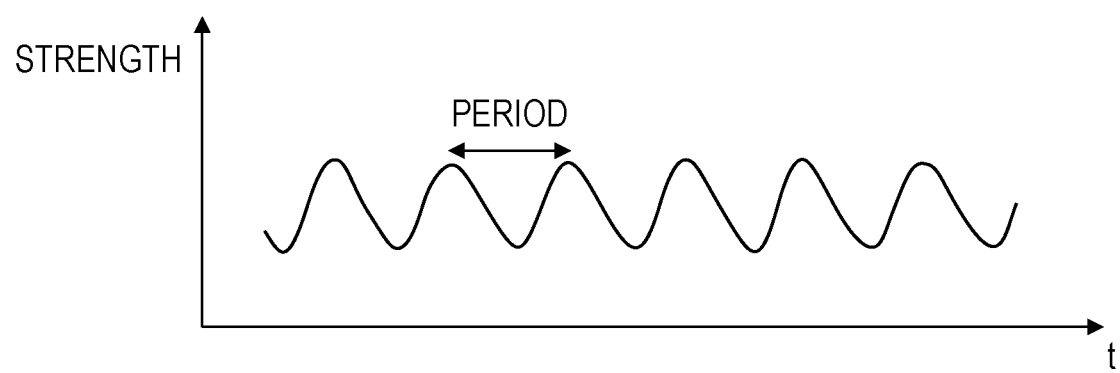
FIG. 8 is a diagram schematically illustrating an example of a pulse wave obtained by measurement.

FIG. 8 is a diagram schematically illustrating an example of a pulse wave obtained by measurement. When a pulse rate is measured, the measurer 230 generates a pulse wave having a periodic curve based on, for instance, the output signal from the light detector 140. For instance, the measurer 230 identifies the local maximum values of pulse waves, and as illustrated, calculates the time difference (referred to as the "period of pulse wave") between two adjacent local maximum values. The measurer 230 calculates a pulse rate by converting the period of pulse wave to a reciprocal.

The estimator 240 of the control circuit 200 measures the variance of the period of pulse wave in a predetermined time period, and can determine a mental state such as a concentrated state or a relaxed state. In general, in a concentrated or nervous state, the period of pulse wave tends to be uniform, whereas in a relaxed state, the period of pulse wave tends to vary. Thus, when the variance of the period is less than a predetermined value, the estimator 240 determines that the subject O is in a concentrated state or in a nervous state. With the breathing, the variance may gradually increase and exceed a predetermined value. In this case, the estimator 240 may determine that the subject O is in a relaxed state.

In addition, aging of blood vessels and a blood pressure can be measured by using the biological information measuring device 100 in a non-contact manner. Specifically, a pulse wave velocity (PWV) is measured by using the biological information measuring device 100. Pulse waves at the face or hand are measured, and PWV is obtained by dividing the distance between them by the time difference between the pulse waves.

For instance, the PWV can be determined by irradiating two exposed test portions of the face and hand with near-infrared light, and detecting reflected light. Alternatively, the PWV can be determined by irradiating, for instance, two exposed test portions of a hand and ankle with near-infrared light, and detecting reflected light. It is to be noted that as two test portions, any points spaced apart may be designated. It is possible to measure aging of blood vessels and a blood pressure based on the PWV in a non-contact manner. According to the above-described flow illustrated in FIG. 5, the control circuit 200 detects initial information of the position information and distance information at two test portions, then sets the initial values of the emission direction of light and the light power to the light source unit 170 based on the initial information. Subsequently, the control circuit 200 adjusts the emission direction of light and the light power according to the movement of the two test portions while monitoring the movement of the test portions during measurement.

Figure 9:
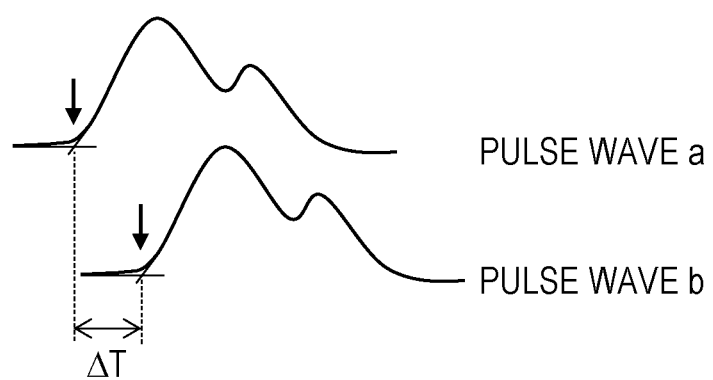
FIG. 9 is a graph schematically illustrating pulse waves obtained from, for instance, two points of the face and hand.

FIG. 9 schematically illustrates pulse waves a, b obtained from, for instance, two points of the face and hand. A measurement point A is positioned on the face and a measurement point B is positioned on a hand. For instance, the measurer 230 of the control circuit 200 calculates PWV from the following Expression (1) using a time difference ΔT between the rising edges (indicated by arrows in FIG. 9) of the pulse waves at the measurement points A and B, and the distance D between the measurement points A and B.

$$PWV = D/\Delta T \qquad \text{Expression (1)}$$

For instance, the estimator 240 of the control circuit 200 can estimate aging of blood vessels and a blood pressure based on the PWV. For instance, a table indicating the average value of PWV for each age (generation) is pre-stored in the ROM 152. The estimator 240 refers to the table to identify the age for which the average PWV value is the closest to the PWV value obtained by the measurement, and can estimate aging of the blood vessels of the subject O. Also, the estimator 240 can estimate a blood pressure from the PWV. For instance, it is possible to utilize the method of estimating a blood pressure using PWV, disclosed in G. Lopez et al. "Continuous blood pressure monitoring in daily life," Journal of Advanced Mechanical Design, Systems, and Manufacturing 3(1), 179-186 (2010).

When a contact measuring instrument is used, how the sensor portion is attached to or pressed against the body may affect to the result of measurement. When measurement is made in a non-contact manner as in this embodiment, such a problem is solved, which leads to simplified measurement.

According to this embodiment, the control circuit 200 adjusts the irradiation position of light and the light power according to the position of and distance to a test portion. Consequently, during the measurement, the subject O is not restrained by the device and can spend time in a relatively relaxed posture. Also, since an appropriate position can be irradiated with light having appropriate power, a high quality signal is obtained. Consequently, the SN ratio can be improved. Furthermore, since the control circuit 200 monitors the movement of the subject O, even when the subject O moves slightly during the measurement, stable measurement of biological information is possible. Therefore, the subject O can undergo measurement while doing some work, for instance.

Second Embodiment

Next, a biological information measuring module in a second embodiment will be described. The biological information measuring module in this embodiment is an attachment that is externally mounted on a general-purpose mobile electronic device such as a tablet terminal, a smartphone, or a notebook PC (laptop), for instance. Hereinafter, the features of the biological information measuring module according to the second embodiment, different from the features of the biological information measuring device 100 in the first embodiment will be mainly described, and a description of common features is omitted.

Figure 10A:
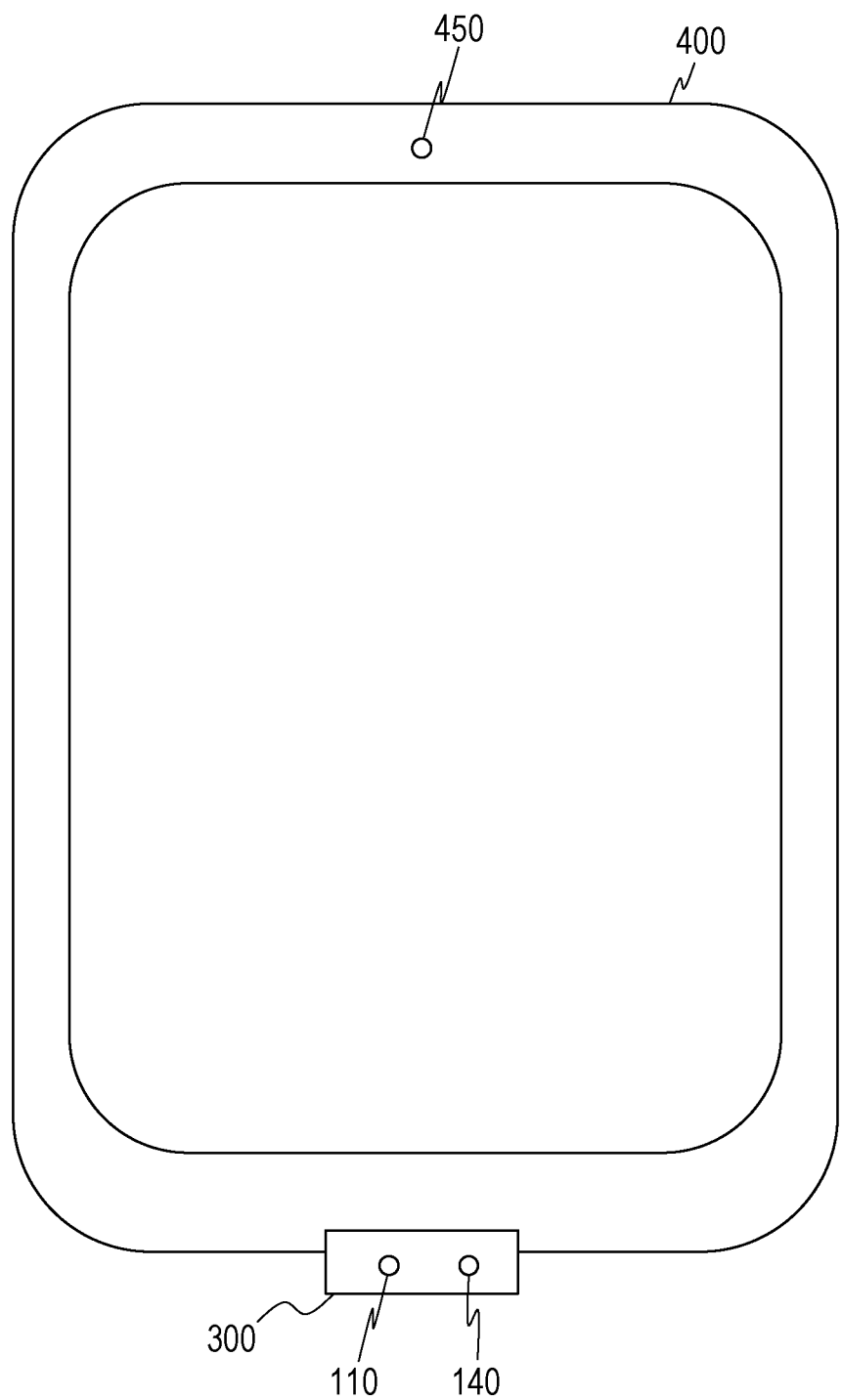
FIG. 10A is a diagram schematically illustrating an example of an electronic device including a biological information measuring module in this embodiment.

FIG. 10A schematically illustrates an example of an electronic device 400 including a biological information measuring module 300 in this embodiment. As illustrated, the biological information measuring module 300 is connected to the electronic device 400 and used. The module 300 has the light source 110 and the light detector 140. Although not illustrated in FIG. 10A, the optical element 120 such as a MEMS mirror, and a control circuit 200A are provided in the case of the module 300. Although the module 300 is connected to a lower portion of the electronic device 400 in the example of FIG. 10A, the embodiment is not limited to this. The position to be connected depends on the position of a connector included in the electronic device 400. In this embodiment, it is possible to utilize the information on moving images obtained by a camera 450 included in the electronic device 400.

This configuration allows a new application method in which the module 300 including, for instance, the light source 110 and the light detector 140 which specializes in biological information measurement (in other words, detects infrared light) is mounted on the electronic device 400 such as a tablet terminal or a smartphone. The following operations may be performed: the built-in camera 450 of the electronic device 400 detects the movement of the subject O, and the control circuit 200A in the module 300 adjusts the emission direction and power of the light source 110 based on a signal detected.

In the built-in camera 450 of a device such as a tablet terminal or a smartphone, the front surface of an image sensor is normally provided with an infrared (IR) cut filter. Therefore, the camera 450 cannot receive infrared light. On the other hand, in order to detect near-infrared light suitable for measurement of biological information, the light detector 140 of the module 300 does not include an IR cut filter but may include a visible light cut filter instead. Therefore, biological information may be detected by the light detector 140 of the module 300, and the position and distance of a test portion, which are detectable even by visible light, may be identified by the camera 450 of the electronic device 400.

Here, the light detector 140 of the biological information measuring module 300 may detect not only biological information, but also the distance between the light source 110 and the test portion. It is possible to detect the position of a test portion by the camera 450 of the electronic device 400. The camera 450, operable with visible light, of the electronic device 400 is operable only by the ambient light without irradiation light from the light source, and the power consumption of the light source is high, thereby providing an effect of reducing the total power consumption of the electronic device.

Figure 10B:
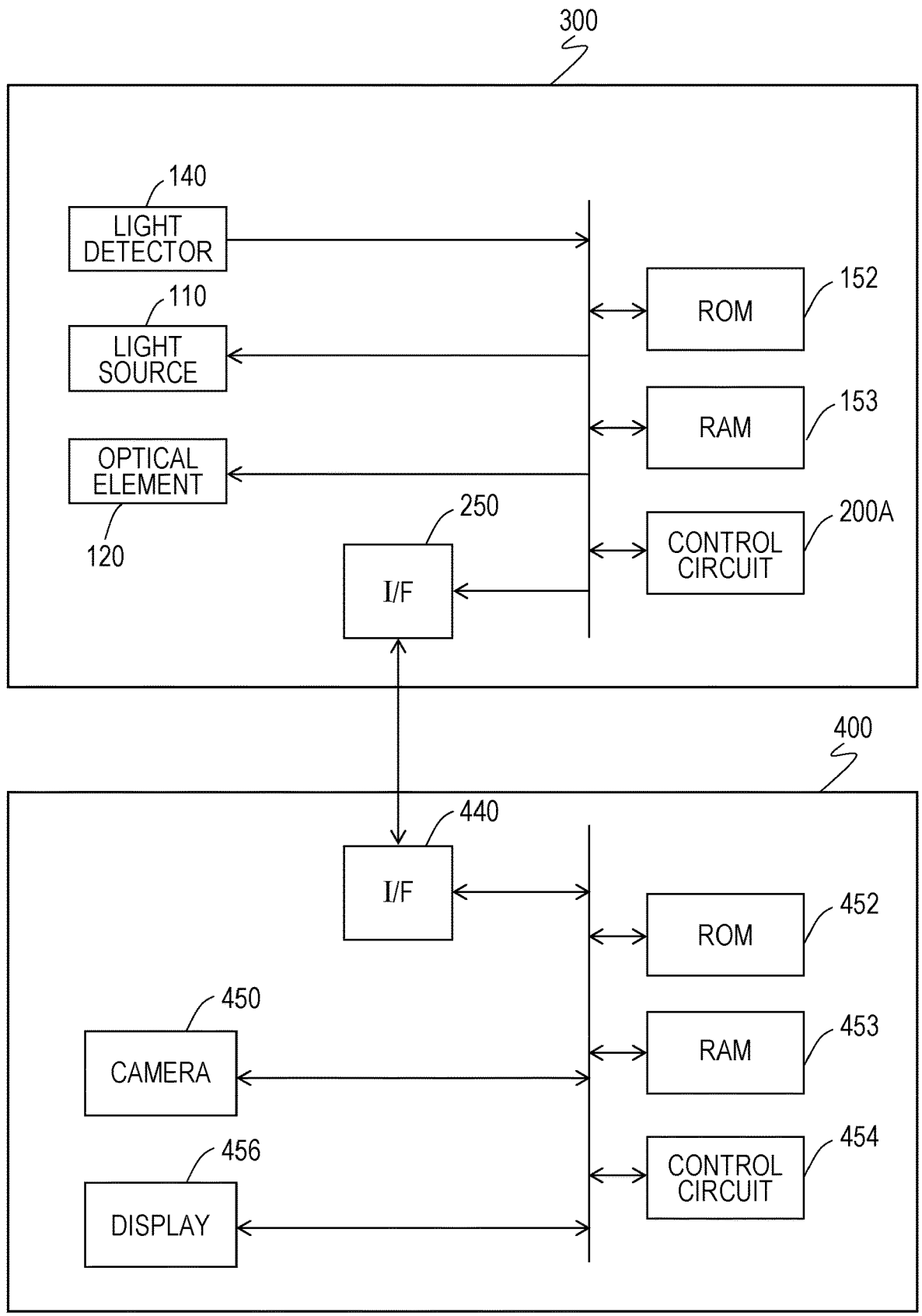
FIG. 10B is a block diagram schematically illustrating the configuration of the biological information measuring module in this embodiment.

FIG. 10B is a block diagram schematically illustrating the configurations of the biological information measuring module 300 and the electronic device 400 in this embodiment. The biological information measuring module 300 has the light source 110, the optical element 120, the optical system 130 (not illustrated), the light detector 140, the control circuit 200A, the ROM 152, the RAM 153, and an input/output interface (I/F) 250 for transmitting an output signal of the light detector 140 to the external electronic device 400. As illustrated, it is sufficient that the module 300 include a minimum number of components to operate as a module.

The electronic device 400 includes a display 456, a control circuit 454, a ROM 452, a RAM 453, and an input/output interface 440 in addition to the camera 450. The control circuit 454 may include a digital signal processor (DSP) for CPU and image processing, for instance. The control circuit 454 analyzes the image obtained by the camera 450, controls displaying of the display 456. The control circuit 454 executes a pre-installed computer program (application), thereby performing an operation in cooperation with the module 300. For instance, the control circuit 454, when performing a measurement operation on biological information, causes the control circuit 200A of the module 300 to measure biological information using the light source 110, the optical element 120, and the light detector 140. At the same time, the control circuit 454 causes the camera 450 to capture the subject O, and calculates the position of and distance to the subject based on the captured image. The control circuit 454 sends the information to the control circuit 200A of the module 300. The control circuit 200A, which has received the information, adjusts the light-emission power of the light source 110 and the angle (in other words, the emission direction of light) of the optical element 120 based on the information on the position and distance. Thus, a test portion is irradiated with light having appropriate power in an appropriate direction while keeping track of the movement of the test portion. The output I/F 250 may be, for instance, a USB interface. The output I/F may be another interface, for instance, an interface for wireless communication in accordance with the Wi-Fi (registered trademark) standard or the ZigBee (registered trademark) standard.

Figure 11:
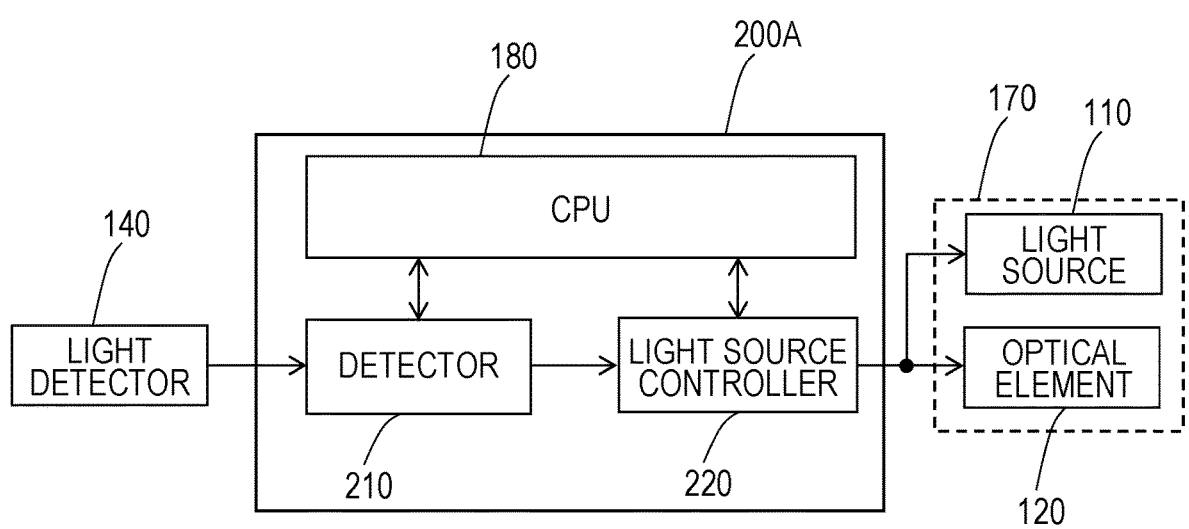
FIG. 11 is a diagram schematically illustrating typical functional blocks of a control circuit of the biological information measuring module.

FIG. 11 is a diagram schematically illustrating typical functional blocks of a control circuit 200A of the biological information measuring module 300. The control circuit 200A has a CPU 180, the detector 210, and the light source controller 220. The control circuit 200A differs from the control circuit 200 of the first embodiment in that the control circuit 200A does not include the measurer 230 and the estimator 240. The CPU 180 controls the operation of the biological information measuring module 300. The function of the detector 210 and the light source controller 220 is as described in the first embodiment.

The biological information measuring module 300 is connectable to the external electronic device 400 via a USB cable connected to the output I/F 250, for instance. An application is installed to the electronic device 400, the application for executing the signal processing (for instance, the above-described processing of measuring the position and distance and processing corresponding to step S502 of FIG. 5) in the present disclosure. Thus, the processor of the electronic device 400 receives an output signal of the light detector 140 from the biological information measuring module 300, and can measure biological information based on the output signal. Also, a mental state of the subject can be estimated based on the biological information.

According to this embodiment, there is provided a biological information measuring module which is detachably attachable to the external electronic device 400.

Third Embodiment

Next, an embodiment of a learning system that uses the technique in the present disclosure will be described.

Figure 12A:
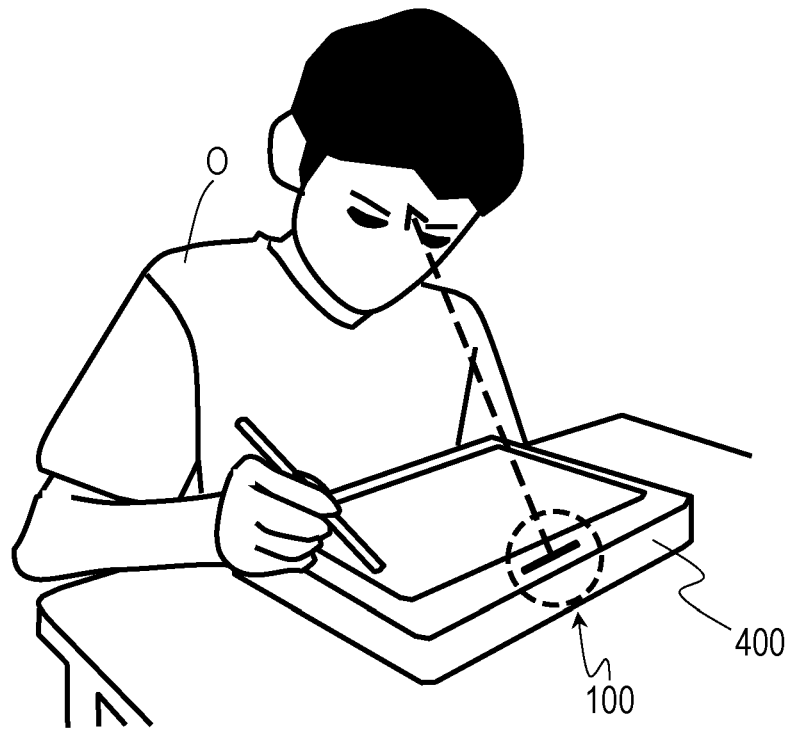
FIG. 12A is an illustration depicting a manner in which a learner as a subject is solving a problem of a subject (for instance, mathematics, national language) using the electronic device.

FIG. 12A is an illustration depicting a manner in which a learner O as a subject is solving a problem of a subject (for instance, mathematics, national language) using the electronic device 400. The electronic device 400 in this embodiment is a tablet-type computer (hereinafter referred to as a tablet PC). In addition to a tablet PC, the electronic device 400 may be any device having a display, such as a mobile phone, a smartphone, a notebook PC (laptop), a digital book terminal, an electronic dictionary, or an electronic note.

The electronic device 400 may be a device to which the module 300 in the third embodiment is mounted, or may be a dedicated terminal in which the function of the module 300 is incorporated.

The education system using a tablet PC as illustrated may be used, for instance, in an educational institution such as a school or a private tutoring school, or a home. The learner O (for instance, pupil) learns using application that displays problems of a subject such as mathematics or national language on a display of a tablet PC.

Application (software), which displays problems of a subject, is pre-installed to the electronic device 400. The application may be downloaded via an electrical communication line such as the Internet. The application is executed by the processor (control circuit) of the electronic device 400, thereby achieving the following operations: displaying a problem, displaying a correct answer and explanation after the problem is answered, and moving on to the next problem.

The control circuit of electronic device 400 in this embodiment monitors the level of concentration of a learner O by detecting biological information such as the cerebral blood flow rate, oxygen saturation in blood, and variance of the period of pulse wave while the learner O is solving a problem. The method of determining a level of concentration is as described in the first embodiment. The control circuit of the electronic device 400, when detecting a decrease in the level of concentration of the learner O, displays information to capture the learner's attention on the display, displays an easy problem, for an instance, to try to avoid decrease in the level of concentration. This can enhance the learning effect.

Figure 12B:
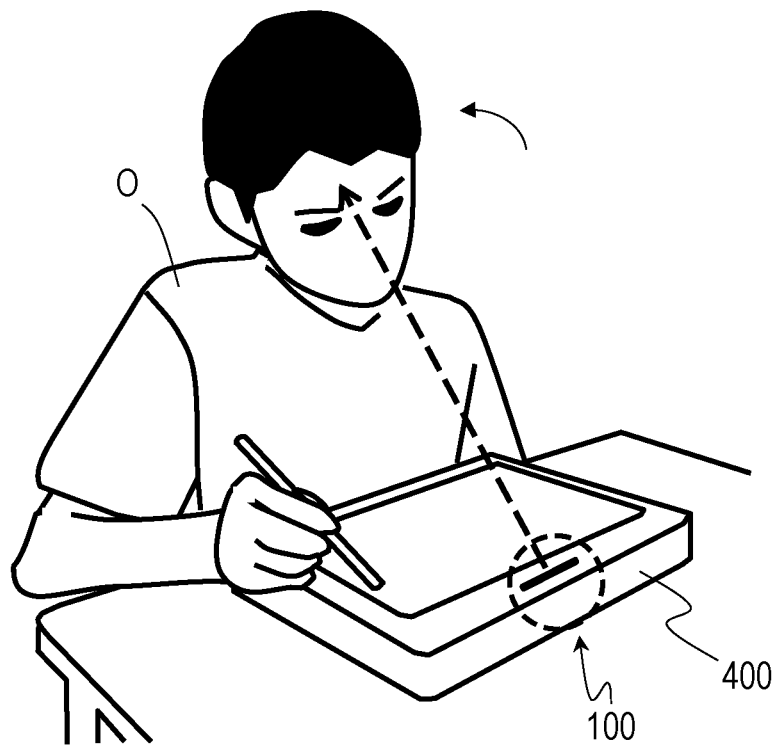
FIG. 12B is an illustration depicting an example of a state where the head of the learner has moved in the state of FIG. 12A.

In the learning system as in this embodiment, the learner O is not necessarily always sitting still while solving a problem. In particular, when the learner O doesn't know how to solve a problem, or lacks concentration, the head and the body of the learner O tend to move. FIG. 12B illustrates an example of a state where the head of the learner O has moved in the state of FIG. 12A. When the head of the learner O moves, the distance between the electronic device 400 and the test portion (forehead) may also change. In such a case, the conventional technique has a problem in that light from a light source does not reach the forehead or even when the light reaches the forehead, the detection accuracy decreases due to a change of the distance.

On the other hand, the control circuit of the electronic device 400 in this embodiment detects the position of the forehead of the learner O, and the distance to the forehead, then adjusts the emission direction and power of light according to the position and the distance. Thus, the forehead of the learner O is irradiated with light having appropriate power, and a level of concentration can be appropriately measured. Such adjustment is made at the start of light-emission of the light source and for every predetermined time during light-emission, thereby making it possible to irradiate with light having appropriate power while keeping track of the movement of the test portion.

The electronic device 400 in this embodiment includes the biological information measuring device 100 in the first embodiment. The electronic device 400 irradiates the forehead of the subject O with infrared light, and estimates a level of concentration in learning of the subject O utilizing the NIRS. The subject O learns by solving a problem displayed on the display screen of the electronic device 400 while manipulating on screen with a stylus. As described above, while the subject O is solving the problem, the cerebral blood flow rate etc. changes according to a level of concentration of the subject O by the activity of nerve cells. The control circuit 200 estimates a level of concentration of the subject O based on the change. For instance, a level of concentration may be determined by referring to a table as described above.

In addition, a level of mastery of learning can be determined by a temporal change of the level of concentration. Description is given by taking learning of factorization in mathematics as an example. At the beginning of learning, a subject learns a factorization formula and application of the formula. In the beginning, since the subject is not getting used to the formula, the level of concentration is high and the amount of temporal change in the cerebral blood flow rate is large. Since the subject gets used to application of the formula, as more problems are solved, the answering time decreases as well as the amount of temporal change in the cerebral blood flow rate decreases. It is possible to determine a mastery level of learning based on the temporal transition of a variation curve of the cerebral blood rate. Use of information indicating a degree of reduction of the answering time in addition to the temporal transition of change in the cerebral blood flow increases the accuracy of determination.

It is expected that the amount of movement of the head of the subject O as a user of the electronic device 400 varies according to the difficulty of the problem. For instance, it is assumed that when the subject O is solving a problem, the angle of the head changes from the angle illustrated in FIG. 12A to the angle illustrated in FIG. 12B. Even in this case, since the control circuit 200 is monitoring the movement of the subject O, detection of a movement enables the emission direction and power of light to be adjusted.

According to this embodiment, even with the subject O doing some work, an appropriate position in the test portion can be irradiated with light having appropriate power and to measure biological information stably.

Fourth Embodiment

Next, an interactive robot in a fourth embodiment will be described.

Figure 13:
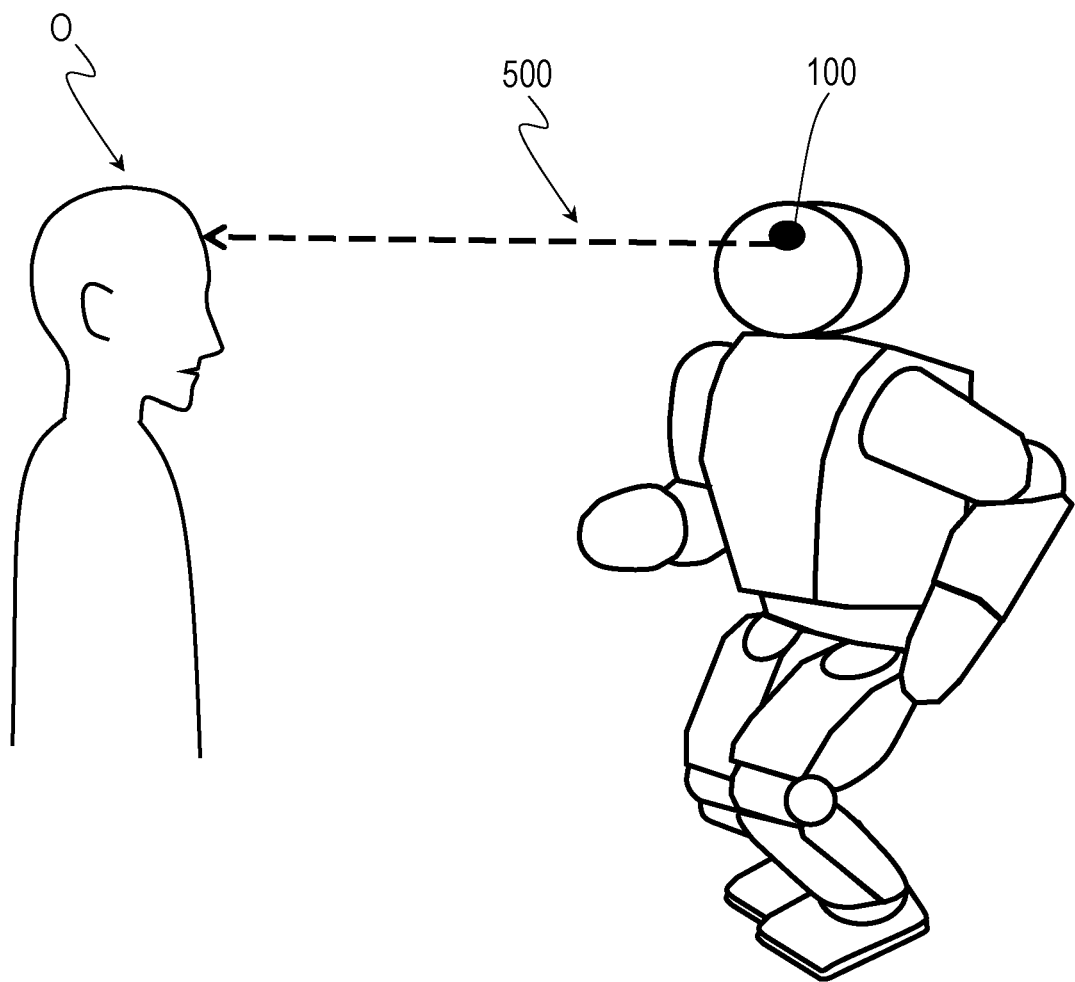
FIG. 13 is an illustration schematically depicting a robot and a conversation partner as a subject.
Figure 14:
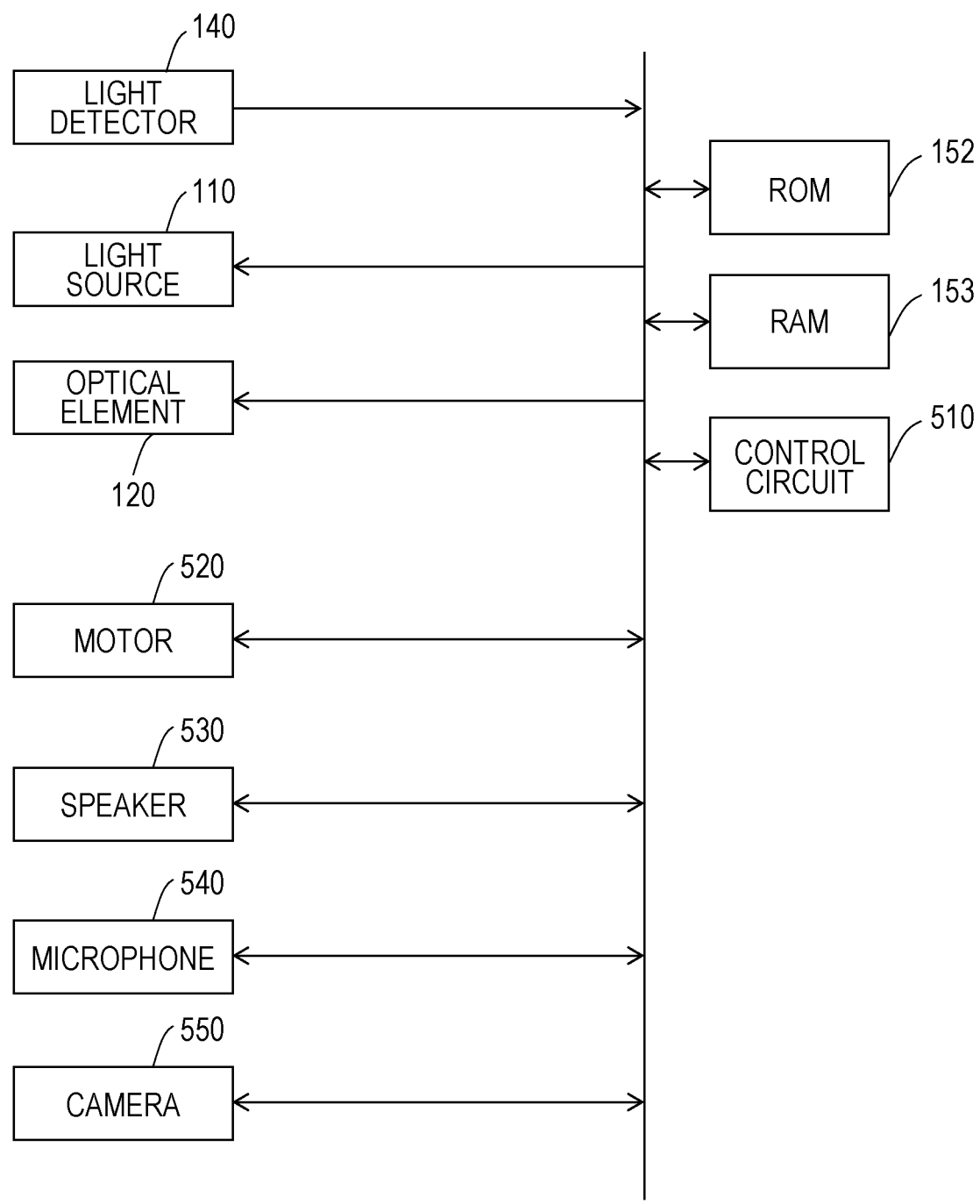
FIG. 14 is a diagram illustrating a configuration example of the robot.

FIG. 13 is an illustration schematically depicting a robot 500 and a conversation partner O as a subject. FIG. 14 is a diagram illustrating a configuration example of the robot 500.

The robot 500 according to this embodiment has a head that includes the same components as in the biological information measuring device 100 in the first embodiment. The robot 500 detects the position and distance of the forehead of the subject O, irradiates the forehead with light having appropriate light power, and estimates the emotion of the subject O utilizing the NIRS. The robot 500 can adjust the irradiation position of light by moving its head while keeping track of the movement of the subject O. Since the robot 500 faces in the direction of the subject O during a conversation, adjusting the irradiation position of light by moving the head is a natural action.

As illustrated in FIG. 14, in addition to the components described in the embodiment, the robot 500 includes at least one motor 520 that drives each part including the head, a speaker 530 that outputs voice, a microphone 540 that detects the voice uttered by the conversation partner O, a camera 550, and a control circuit 510 that controls each part. The control circuit 510 detects the position of a test portion (for instance, the forehead) of the conversation partner O and the distance to the test portion by performing the same operations as those of the control circuit 200 in the first embodiment. The control circuit 510 then measures biological information such as the cerebral blood flow rate based on a result of the detection of the light detector 140. The control circuit 510 then generates a control signal for controlling an element such as the motor 520 and the speaker 530 based on the biological information. The robot 500 can perform various operations based on the control signal. For instance, when a decrease in the level of concentration of the conversation partner O is detected during a voice conversation using the speaker 530 and the microphone 540, the subject of the conversation may be changed or the voice conversation may stopped. During a conversation, the robot 500 estimates the emotion of the conversation partner O. Specifically, the control circuit 510 estimates the emotion based on a change in the cerebral blood flow caused by neural activity. For instance, the control circuit 510 can estimate the emotion by referring to a table that associates a change in the cerebral blood flow with an emotion (such as relief, anxiety, sadness, anger). The robot 500 can change the subject with the conversation partner, for instance, according to a result of the estimation of the emotion.

The control circuit 510 can adjust the emission direction of light by controlling the movement of the head according to the position of and distance to the test portion. Furthermore, the emission direction of light may be controlled by combining the head of the robot 500 and the optical element 120 disposed in front of the light source 110. For instance, the movement of the head is first controlled to generally adjust the emission direction of light, then the light source unit 170 is controlled, and the emission direction of light can be finely adjusted. The optical element 120 may not be provided if unnecessary.

A program (application), which defines the operations of this embodiment, is downloaded, for instance, via an electrical communication line and may be installed to the robot 500. Thus, the operation can also be improved by updating the application.

According to this embodiment, appropriate communication can be established in a conversation with a robot.

Fifth Embodiment

Figure 15:
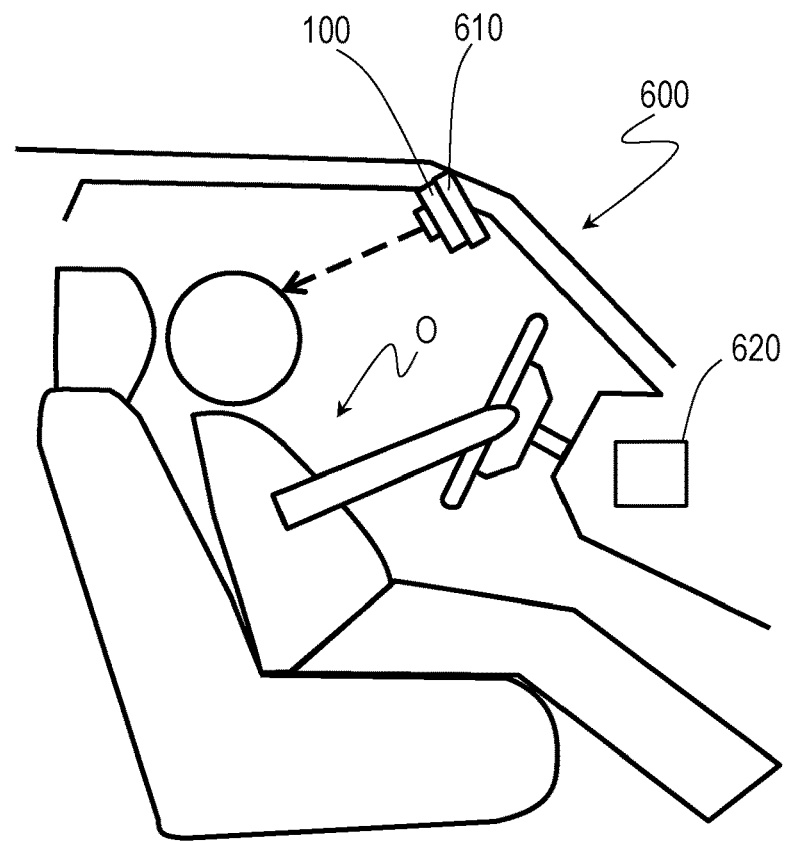
FIG. 15 schematically illustrates the inside of a vehicle according to a fifth embodiment.

FIG. 15 schematically illustrates the inside of a vehicle 600 according to a fifth embodiment.

The vehicle 600 according to this embodiment includes a biological information measuring device 100 in the embodiment at a position or its vicinity where, for instance, a drive recorder is attached. The biological information measuring device 100 may be attached to an attachment portion 610 of the vehicle 600. A driver can attach or detach the biological information measuring device 100 freely. The vehicle 600 refers to not only an automobile but also a mobile object which needs to be operated, such as a train and others. In this embodiment, the subject O is a driver.

The biological information measuring device 100 irradiates the forehead of the subject O with infrared light, and estimates a level of concentration and physical condition of the subject O utilizing the NIRS. The vehicle 600 includes a control circuit 620 that controls the operation of the vehicle 600. The control circuit 620 generates a control signal of the vehicle 600 based on the biological information from the control circuit 200 of the biological information measuring device 100. Alternatively, the control circuit 200 may generate a control signal of the vehicle 600 based on the biological information, and the control circuit 620 may control the vehicle 600 based on the control signal. The vehicle has an automatic operation mode, for instance. During driving of the vehicle by manual operation, the vehicle receives a control signal, and can switch the driving mode from manual operation to automatic operation. For instance, when a decrease in the level of concentration of the driver O is detected, the driver O may be drowsy. Thus, switching from manual operation to automatic operation ensures the safety.

It is also possible to operate the biological information measuring device 100 in conjunction with a car navigation system. For instance, the biological information measuring device 100, when determining that the driver lacks concentration, can transmit relevant information to the car navigation system. The car navigation system can warn of the lack of concentration using a voice speaker or a display screen, for instance. It is to be noted that the biological information measuring device 100 does not need to irradiate the driver with infrared light all the time, and for instance, a direction (such as "turn right at the intersection 100 m ahead") of the car navigation system may trigger the biological information measuring device 100 to irradiate the driver with infrared light to determine the concentration level of the driver. When no change in the cerebral blood flow is detected even after voice directions are given by the car navigation, it is highly probable that the driver lacks concentration.

Sixth Embodiment

Figure 16:
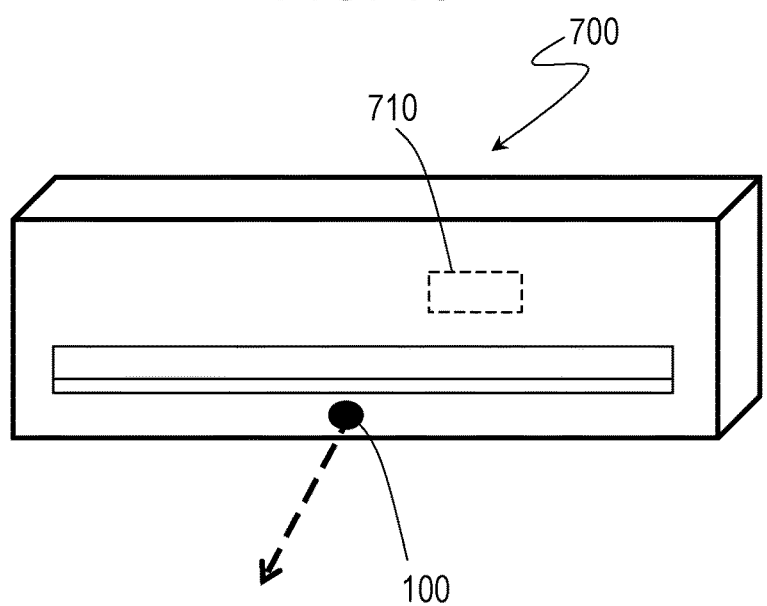
FIG. 16 schematically illustrates the external appearance of an environmental control device according to a sixth embodiment.

FIG. 16 schematically illustrates the external appearance of an environmental control device 700 according to a sixth embodiment.

The environmental control device 700 according to this embodiment includes the biological information measuring device 100. The environmental control device 700 may be an air conditioner or an audio, for instance. A device capable of controlling such surrounding environment (such as temperature, sound, light, humidity, smell) of a user is referred to as an "environmental control device" in the present description. In this embodiment, the subject O may be one or a plurality of users of the environmental control device 700.

The environmental control device 700 irradiates the forehead of the subject O with infrared light, and estimates a mental state, specifically, the feeling and temperature sensation of the subject O using the NIRS.

The control circuit 200 of the biological information measuring device 100 monitors the movement of the subject O, and identifies the subject O first. Subsequently, the control circuit 200 identifies the position of a test portion (for instance, forehead) of the subject O by image recognition, and starts to irradiate the forehead with infrared light.

The environmental control device 700 includes a control circuit 710. The control circuit 710 generates a control signal of the environmental control device 700 based on the biological information from the control circuit 200 of the biological information measuring device 100. Alternatively, the control circuit 200 may generate a control signal of the environmental control device 700 based on the biological information, and the control circuit 710 may control the environmental control device 700 based on the control signal. For instance, it is assumed that the biological information measuring device 100 has detected discomfort of the subject O. In the case where the environmental control device 700 is an air conditioner, the environmental control device 700 can automatically turn on the power supply to start the operation or decrease or increase the preset temperature during the operation. In the case where the environmental control device 700 is an audio device, the environmental control device 700 may automatically turn the sound volume down, and may automatically select a music piece (such as a classical music piece) which is expected to provide a relaxing effect, for instance.

Seventh Embodiment

The features of a biological information measuring device according to a seventh embodiment, different from the features of the biological information measuring device 100 in the first embodiment will be mainly described.

The case is discussed where the irradiation light from the light source 110 is not parallel light but diverging light. The inventor of the present application has discovered that when the entire test portion is irradiated with diverging light to obtain an image of the test portion by an image sensor, detection of a brightness variation in the test portion provides a higher accuracy of detection of the presence of movement of the subject than the detection of the distance between the light source 110 and the test portion. Specifically, the biological information measuring device 100 in the seventh embodiment differs from the biological information measuring device 100 of the first embodiment in that a brightness variation is detected.

Specifically, compared with the first embodiment, the light detector 140 is an image sensor, and the operations of the processing steps S503 to S506 illustrated in FIG. 5 are different.

Hereinafter, the operation of step S503 in the seventh embodiment will be described under the assumption that the operations are predominantly performed by the control circuit 200 which executes the function corresponding to each functional block. As described above, when a CPU is provided independently from the control circuit 200, the CPU may execute part of the function of the control circuit 200. Hereinafter, a description is given under the assumption that the light detector 140 is a TOF image sensor and the optical element 120 is a MEMS mirror.

The detector 210 extracts a first brightness from an image of the tested portion obtained at a first time in the light detector 140, and extracts a second brightness from an image of the tested portion obtained at a second time in the light detector 140. The control circuit 200 calculates a brightness variation in the test portion between the first time and the second time based on the first brightness and the second brightness. When the magnitude of the brightness variation is greater than or equal to a threshold value, the detector 210 determines that the subject O has moved, and when the magnitude of the brightness variation is less than the threshold value, the detector 210 determines that the subject O has not moved. For instance, the threshold value is pre-stored in the ROM 152.

In the seventh embodiment, since the distance between the light source 110 and the test portion is not directly measured, step S505 in the first embodiment is unnecessary. After the brightness variation is calculated, the processing proceeds to step S506. In step S506, a drive current variation amount ΔJ of the light source 110 is determined according to the detected brightness variation. When the drive current of the light source 110 at the first time is J1, the drive current of the light source 110 at the second time is set to J2=J1+ΔJ. When the irradiation light is diverging light, the brightness variation is detectable with high accuracy, and thus the accuracy of the drive current variation amount ΔJ of the light source 110 can be increased, and adjustment accuracy of the power of light can be improved.

Here, the brightness extracted from an image of the test portion may be an average value of brightness of the entire test portion. However, when the distance from the light source 110 to the test portion varies, the accuracy of detection of the brightness variation is high, provided that the variation in the distance is small. Thus, when the initial light power of the light source 110 is determined, the distance from the light source 110 to the test portion is actually detected, and when the light power of the light source 110 is adjusted by the movement of the test portion after the initial light power of the light source 110 is determined, the brightness variation may be detected.

Eighth Embodiment

The features of a biological information measuring device according to an eighth embodiment, different from the features of the biological information measuring device 100 in the first embodiment will be mainly described.

The biological information measuring device 100 in the eighth embodiment differs from the biological information measuring device 100 of the first embodiment in that a distance variation is detected.

Specifically, compared with the first embodiment, the operations of the processing steps from S503 to S506 illustrated in FIG. 5 are different.

Hereinafter, the operation of step S503 in the eighth embodiment will be described under the assumption that the operations are predominantly performed by the control circuit 200 which executes the function corresponding to each functional block. As described above, when a CPU is provided independently from the control circuit 200, the CPU may execute part of the function of the control circuit 200. Hereinafter, a description is given under the assumption that the light detector 140 is a TOF image sensor and the optical element 120 is a MEMS mirror.

In step S503 of the eighth embodiment, the detector 210 obtains a first distance between the light source 110 and the test portion at a first time, and obtains a second distance between the light source 110 and the test portion at a second time. A distance variation between the first time and the second time is calculated based on the obtained first distance and second distance.

When the magnitude of the distance variation is greater than or equal to a threshold value, the detector 210 determines that the subject O has moved, and when the magnitude of the distance variation is less than the threshold value, the detector 210 determines that the subject O has not moved. For instance, the threshold value is pre-stored in the ROM 152.

In the eighth embodiment, when it is determined that the subject O has moved, the distance between the light source 110 and the test portion does not need to be detected again, and thus step S505 is unnecessary. That is, when it is determined that the subject O has moved, a drive current variation amount ΔJ of the light source is determined according to the calculated distance variation.

When the drive current of the light source at the first time is J1, the drive current of the light source at the second time is set to J2=J1+ΔJ. In general, ΔJ is sufficiently smaller than J1, thus an upper limit, which is sufficiently smaller value than J1, may be set to the variation ΔJ. Thus, even when an error occurs in detection of a distance, a drive current variation amount due to the detection error is small, and thus it is possible to reduce malfunction of the light source, such as irradiation with light power other than predetermined power.

What is claimed is:

1. A biological information measuring device comprising:
a light source that, in operation, emits irradiation light for irradiating a test portion of a subject;
at least one light detector that, in operation, detects light from the subject and outputs an electrical signal corresponding to the light; and
a control circuit that, in operation, determines a power of the irradiation light emitted by the light source, and that, in operation, measures biological information related to a blood flow at the test portion based on the electrical signal, wherein, in operation,
the control circuit detects a distance between the light source and the test poliion based on the electrical signal, and determines the power of the irradiation light such that the power of the irradiation light is increased as the distance increases, and
relative movement of the test portion with respect to the light source causes the distance between the light source and the test portion to change, and
wherein the light source is stationary during a testing process, and the distance between the test portion and the light source is variable during the testing process due to movement of the test portion.

2. The biological information measuring device according to claim 1, wherein, in operation,
the control circuit further compares a first distance that is the distance at a first time during
the testing process with a second distance that is the distance at a second time during the testing process, and after the first time, and when it is determined that the distance has changed as a result of the comparison, the control circuit determines the power of the irradiation light again.

3. The biological information measuring device according to claim 2, wherein
the at least one light detector is an image sensor that, in operation, obtains a moving image of the test portion, the moving image including a plurality of frames, and
the control circuit, in operation, makes the comparison between the first distance and the second distance for every predetermined number of frames in the plurality of frames.

4. The biological information measuring device according to claim 2, wherein, in operation,
the control circuit further determines whether or not a result of the measuring of the biological information is below a threshold, and when it is detected that the result of the measuring is below the threshold, the control circuit makes the comparison between the first distance and the second distance.

5. The biological information measuring device according to claim 1, wherein
the at least one light detector is an image sensor that, in operation, obtains an image of the test portion,
the electrical signal includes a signal representing the image, and
based on the signal representing the image, the control circuit, in operation, detects a first brightness that is a brightness of the test portion at a first time, a second brightness that is a brightness of the test portion at a second time after the first time, and a brightness variation amount which is a difference between the first brightness and the second brightness, and the control circuit, in operation, adjusts the power of the irradiation light based on the brightness variation amount.

6. The biological information measuring device according to claim 5, wherein
the image is a moving image including a plurality of frames, and
the control circuit, in operation, detects the brightness variation amount for every predetermined number of frames in the plurality of frames.

7. The biological information measuring device according to claim 5, wherein, in operation,
control circuit further determines whether or not a result of the measuring of the biological information is below a threshold, and when it is detected that the result of the measuring is below a threshold, the control circuit detects the brightness variation amount.

8. The biological information measuring device according to claim 1, wherein, in operation,
the control circuit further detects a distance variation amount which is a difference between a first distance that is the distance at a first time and a second distance that is the distance at a second time after the first time, and the control circuit adjusts the power of the irradiation light based on the distance variation amount.

9. The biological information measuring device according to claim 8, wherein
the image is a moving image including a plurality of frames, and
the control circuit, in operation, detects the distance variation amount for every predetermined number of frames in the plurality of frames.

10. The biological information measuring device according to claim 8, wherein, in operation,
the control circuit further determines whether or not a result of the measuring of the biological information is below a threshold, and when it is detected that the result of the measuring is below a threshold, the control circuit detects the distance variation amount.

11. The biological information measuring device according to claim 1, wherein, in operation,
the control circuit further detects a position of the test portion based on the electrical signal, and determines an irradiation position of the irradiation light in the subject based on the position of the test portion.

12. The biological information measuring device according to claim 11, wherein
the at least one light detector is an image sensor that, in operation, obtains an image of the test portion,
the electrical signal includes a signal representing the image, and
the control circuit, in operation, detects a position of the test portion by image recognition based on the signal representing the image.

13. The biological information measuring device according to claim 1, wherein
the at least one light detector includes a first light detector and a second light detector, the first light detector and the second light detector are provided in the biological information measuring device,
the second light detector is an image sensor,
the first light detector, in operation, detects a first component which is a component of a wavelength included in the irradiation light out of the light from the subject, and outputs a first electrical signal corresponding to the first component,
the second light detector, in operation, detects a second component which is a component of visible light out of the light from the subject, and outputs a second electrical signal corresponding to the second component, and
the control circuit, in operation, detects the distance based on the second electrical signal, and measures the biological information based on the first electrical signal.

14. The biological information measuring device according to claim 11, further comprising:
an optical element that is disposed on a path of the irradiation light and that, in operation, changes the irradiation position, wherein, in operation,
the control circuit controls the optical element based on the electrical signal.

15. The biological information measuring device according to claim 1, wherein
the test portion is a forehead of the subject, and
the biological information is information related to a cerebral blood flow.

16. The biological information measuring device according to claim 1, further comprising:
an interface that, in operation, transmits the electrical signal outputted from the at least one light detector to an external device.

17. A biological information measuring device comprising:
a light source that, in operation, emits irradiation light for irradiating a test portion of a subject;
at least one light detector that, in operation, detects light from the subject and outputs a first electrical signal corresponding to the light;
a control circuit that, in operation, determines a power of the irradiation light emitted by the light source, and measures biological information related to a blood flow at the test portion based on the first electrical signal; and
an interface that, in operation, communicates with an external device including an image sensor that, in operation, obtains an image of the test portion and outputs a second electrical signal including a signal representing the image, wherein, in operation,
the interface receives the second electrical signal from the external device, and transmits the first electrical signal to the external device,
the control circuit detects a distance between the light source and the test portion based on the second electrical signal, and determines the power of the irradiation light such that the power of the irradiation light is increased as the distance increases,
relative movement of the test portion with respect to the light source causes the distance between the light source and the test portion to change, and
wherein the light source is stationary during a testing process, and the distance between the test portion and the light source is variable during the testing process due to movement of the test portion.

18. The biological information measuring device according to claim 1, wherein
the control circuit detects the distance between the light source and the test portion based on a difference between a phase of the irradiation light and a phase of the light detected by the at least one light detector.

* * * * *